(12) United States Patent
Trehan

(10) Patent No.: US 11,996,090 B2
(45) Date of Patent: May 28, 2024

(54) SYSTEM AND METHOD FOR ARTIFICIAL INTELLIGENCE (AI) ASSISTED ACTIVITY TRAINING

(71) Applicant: Rajiv Trehan, Bangkok (TH)

(72) Inventor: Rajiv Trehan, Bangkok (TH)

(73) Assignee: Rajiv Trehan, Bangkok (TH)

( * ) Notice: Subject to any disclaimer, the term of this patent is extended or adjusted under 35 U.S.C. 154(b) by 324 days.

(21) Appl. No.: 17/467,386

(22) Filed: Sep. 6, 2021

(65) Prior Publication Data

US 2022/0076666 A1 Mar. 10, 2022

Related U.S. Application Data

(60) Provisional application No. 63/074,539, filed on Sep. 4, 2020.

(51) Int. Cl.
  *A61B 5/02* (2006.01)
  *A63B 24/00* (2006.01)
  *A63B 71/06* (2006.01)
  *G06N 20/00* (2019.01)
  *G06V 40/20* (2022.01)
  *G10L 15/18* (2013.01)
  *G10L 15/22* (2006.01)

(52) U.S. Cl.
  CPC .......... *G10L 15/18* (2013.01); *A63B 24/0006* (2013.01); *A63B 24/0062* (2013.01); *A63B 24/0075* (2013.01); *A63B 24/0087* (2013.01); *A63B 71/0622* (2013.01); *G06N 20/00* (2019.01); *G06V 40/23* (2022.01); *G10L 15/22* (2013.01); *A63B 2024/0009* (2013.01); *A63B 2024/0015* (2013.01); *A63B 2024/0071* (2013.01); *A63B 2024/0096* (2013.01); *A63B 2071/0627* (2013.01); *A63B 2220/806* (2013.01); *A63B 2225/12* (2013.01)

(58) Field of Classification Search
  USPC .............................................................. 704/9
  See application file for complete search history.

(56) References Cited

U.S. PATENT DOCUMENTS

| | | | | |
|---|---|---|---|---|
| 11,202,579 B2* | 12/2021 | Freeman | ............ | A61B 5/14542 |
| 11,738,237 B2* | 8/2023 | Shavit | .................... | A63B 21/16 |
| | | | | 482/5 |
| 2010/0222179 A1* | 9/2010 | Temple | .............. | A63B 71/0622 |
| | | | | 482/8 |

(Continued)

*Primary Examiner* — Marcellus J Augustin

(57) ABSTRACT

The disclosure relates to system and method for Artificial Intelligence (AI) assisted activity training. The method includes presenting a plurality of activity categories to a user and receiving a voice-based input from the user. The method uses a Natural Language Processing (NLP) model to process the received voice-based input to extract the selection of at least one activity and at least one activity attribute. Contemporaneous to receiving voice-based input, the method presents a multimedia content in conformance with one activity and one activity attribute. In response to initiation of the multimedia content, the method further detects initiation of a user activity performance. The method captures a video of the user activity and process the video using an AI model to extract a set of user performance parameters. Further, a feedback may be generated based on differential between the set of user performance parameters and a target set of performance parameters.

19 Claims, 21 Drawing Sheets

(56) References Cited

U.S. PATENT DOCUMENTS

| | | | | |
|---|---|---|---|---|
| 2014/0315610 | A1* | 10/2014 | Shachar | G06T 7/20 |
| | | | | 463/7 |
| 2017/0310664 | A1* | 10/2017 | Satkunarajah | H04L 63/0861 |
| 2018/0165854 | A1* | 6/2018 | Du | G06F 16/00 |
| 2021/0110737 | A1* | 4/2021 | Kamath | G06Q 30/0282 |
| 2021/0342952 | A1* | 11/2021 | Putnam | A63B 71/0622 |

* cited by examiner

FIG. 5

FIG. 9C

SYSTEM AND METHOD FOR ARTIFICIAL INTELLIGENCE (AI) ASSISTED ACTIVITY TRAINING

CROSS-REFERENCE TO RELATED APPLICATION

This application claims priority benefits under 35 U.S.C. § 119(e) to U.S. Provisional Application No. 63/074,539 filed on Sep. 4, 2020, which is hereby incorporated by reference in its entirety.

TECHNICAL FIELD

This disclosure relates generally to system and method for providing activity training, and more particularly to system and method for Artificial Intelligence (AI) assisted activity training.

BACKGROUND

Over the last couple of years, people have been increasingly aspiring to be healthy and have normal levels of fitness, while maintaining work and personal life balance. Moreover, desire to manage their own health has been increasing. As a result, exercising after work, while travelling, on weekends, or in free time, has been on the rise. There are a variety of physical activities (for example, strength training, dance, yoga, Pilates, martial arts, boxing, meditation, physical therapy and rehabilitation, CrossFit, Les Mills, F45, Zumba, Bikram Yoga, Orange Theory, or other types of workouts or exercises) that may be performed to improve quality of life with a little investment of time. Moreover, there are a lot of facilities and provisions that facilitate user's access to such variety of physical activities. Notwithstanding, many people do not want to travel and visit exercise facilities, gyms, physical rehabilitation centers, dojos, martial arts centers, dance studios as they do not have time and/or motivation. Another reasons may be affordability, as some people may not be able to afford personal instructions provided by trained experts. Recent pandemic has also made people worried about visiting such facilities because of potential virus and communicative illnesses. Physical disabilities may be another factor that may discourage people from travelling to and using such facilities.

As a result of the aforementioned issues, many people have started exercising or performing other activities in the comfort of their home or room (for example, hotel room). Indoor performance of physical activities has been resonating with many people, since a person's schedule, weather, or other limiting factors as mentioned above can be easily circumvented. Accordingly, sale of indoor exercise apparatuses, such as, treadmills, stair exerciser apparatuses, steppers, exercise bikes, elastic bands, and other similar motion exerciser apparatuses has increased.

For best results of such physical activities and to reduce the chance of muscle damage and injuries, many such physical activities require a user to correctly perform complex actions entailed therein. Additionally, skilled adjustment of weights or force resistance may also be of importance. Thus, unless the user has an expert to analyze the pose and movements of the user, the user may perform one or more actions with improper pose and movements, thereby injuring himself. Moreover, in the long run, performing such physical activities indoors may get mundane and boring, as trainers or peers are not present to motivate or encourage the user to keep performing. As a result, the user may get discouraged and may either become irregular or may completely stop performing any physical activity.

Therefore, there is a need for methods and systems that assist users in performing physical activities indoors under expert guidance and monitoring, while being convenient and cost effective.

SUMMARY

In an embodiment, a method for Artificial Intelligence (AI) assisted activity training is disclosed. The method may present, via a rendering device, a plurality of activity categories to a user. Each of the plurality of activity categories may include a plurality of activities. The plurality of activity categories may be presented as multimedia content. The method may receive a voice-based input from the user. The voice-based input may include an activity training plan comprising a selection of at least one activity from at least one of the plurality of activity categories and at least one activity attribute associated with each of the at least one activity. Further, the voice-based input may be in a source language. The method may process the received voice-based input using a Natural Language Processing (NLP) model to extract the selection of at least one activity and the at least one activity attribute. The NLP model may be configured using a single language and the single language may be an intermediate language, which may be used by the method to process user instructions. Contemporaneous to receiving the voice-based input, the method may initiate presentation of a multimedia content in conformance with the at least one activity and the at least one activity attribute. The multimedia content may include a plurality of guidance steps performed by a virtual assistant corresponding to the at least one activity. Further, an initiation of a user activity performance of the user may be detected in response to initiation of the multimedia content. The user activity performance of the user at a given time may include imitation of one of the at least one activity. The method may capture, via the at least one camera, a video of the user activity performance of the user. The at least one camera may be placed at distributed locations. Further, the method may process, in-real time, using an Artificial Intelligence (AI) model, the video to extract a set of user performance parameters of the user based on the user activity performance. The method may generate, by the AI model, a feedback based on differential between the set of user performance parameters and a target set of performance parameters. Further, the method may render, contemporaneous to the user activity performance, the feedback to the user in at least one of an aural form, a visual form, or as a haptic feedback.

In another embodiment, a system for Artificial Intelligence (AI) assisted activity training is disclosed. The system may include a processor, and a memory communicatively coupled to the processor. The memory includes processor instructions, which when executed by the processor causes the processor to present, by a rendering device, a plurality of activity categories to a user. Each of the plurality of activity categories may include a plurality of activities. The plurality of activity categories may be presented as multimedia content. The processor instructions may receive a voice-based input from the user. The voice-based input may include an activity training plan comprising a selection of at least one activity from at least one of the plurality of activity categories and at least one activity attribute associated with each of the at least one activity. The voice-based input may be in a source language. Further, the processor instructions, may processes the received voice-based input using a Natural Language Processing (NLP) model to extract the selection of at least one activity and the at least one activity attribute. The NLP model may be configured using a single language and the single language may be an intermediate language, which may be used by the system to process user instructions. Contemporaneous to receiving the voice-based input, the processor instructions may initiate presentation of a multimedia content in conformance with the at least one activity and the at least one activity attribute. The multimedia content may include a plurality of guidance steps performed by a virtual assistant corresponding to the at least one activity. Further, an initiation of a user activity performance of the user may be detected in response to initiation of the multimedia content. The user activity performance of the user at a given time may include imitation of one of the at least one activity. The processor instructions may capture, via the at least one camera, a video of the user activity performance of the user. The at least one camera may be placed at distributed locations. Further, the processor instructions may process, in-real time, using an Artificial Intelligence (AI) model, the video to extract a set of user performance parameters of the user based on the user activity performance. The processor instructions may generate, by the AI model, a feedback based on differential between the set of user performance parameters and a target set of performance parameters. Further, the processor instructions may render, contemporaneous to the user activity performance, the feedback to the user in at least one of an aural form, a visual form, or as a haptic feedback.

In yet another embodiment, a computer program product for Artificial Intelligence (AI) assisted activity training is disclosed. The computer program product is embodied in a non-transitory computer readable storage medium and comprises computer instructions for presenting, by a rendering device, a plurality of activity categories to a user. Each of the plurality of activity categories may include a plurality of activities. The plurality of activity categories may be presented as multimedia content. The computer instructions may receive a voice-based input from the user. The voice-based input may include an activity training plan comprising a selection of at least one activity from at least one of the plurality of activity categories and at least one activity attribute associated with each of the at least one activity. Further, the voice-based input may be in a source language. The computer instructions may process the received voice-based input using an NLP model to extract the selection of at least one activity and the at least one activity attribute. The NLP model may be configured using a single language and the single language may be an intermediate language, which may be used by the computer program product to process user instructions. Contemporaneous to receiving the voice-based input, the computer instructions may initiate presentation of a multimedia content in conformance with the at least one activity and the at least one activity attribute. The multimedia content may include a plurality of guidance steps performed by a virtual assistant corresponding to the at least one activity. Further, an initiation of a user activity performance of the user may be detected in response to initiation of the multimedia content. The user activity performance of the user at a given time may include imitation of one of the at least one activity. The computer instructions may capture, via the at least one camera, a video of the user activity performance of the user. The at least one camera may be placed at distributed locations. Further, the computer instructions may process, in-real time, using an Artificial Intelligence (AI) model, the video to extract a set of user performance parameters of the user based on the user activity performance. The computer instructions may generate, by the AI model, a feedback based on differential between the set of user performance parameters and a target set of performance parameters. Further, the computer instructions may render, contemporaneous to the user activity performance, the feedback to the user in at least one of an aural form, a visual form, or as a haptic feedback.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

FIG. 5 illustrates a Graphical User Interface (GUI) depicting a plurality of activity categories for AI assisted activity training, in accordance with some exemplary embodiments.

FIGS. 9A-9D illustrate GUIs depicting creation of a new activity training circuit and subsequent saving of the activity training circuit as a playlist, in accordance with some exemplary embodiments.

DETAILED DESCRIPTION

Exemplary embodiments are described with reference to the accompanying drawings. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims. Additional illustrative embodiments are listed below.

Figure 1:
FIG. 1 illustrates an exemplary smart mirror for providing an Artificial Intelligence (AI) assisted activity training, in accordance with some embodiments.

Referring now to FIG. 1, a smart mirror 100 for providing an Artificial Intelligence (AI) assisted activity training to a user 102 is illustrated, in accordance with some embodiments. The user 102 may be undergoing the AI assisted activity training within the comfort of his room. The smart mirror 100 may be a half mirror with a hidden or partially hidden display or may be a one-way mirror having an integrated display screen. The smart mirror 100 may have an external appearance of an actual mirror that has the display screen integrated within. The smart mirror 100 may have at least a partially covered semi-reflective coating or an integrated mirror. The semi-reflective coating or the integrated mirror may reflect an image of the user 102 while simultaneously allowing display and viewing of videos or information presented via the display screen of the smart mirror 100.

The smart mirror 100 may include a system that is configured to provide AI assisted activity training to a user 102. The system and various components within the system have been explained in detail in conjunction with FIG. 4. Once the user 102 activates or initiates the smart mirror 100, the user 102 may be presented with a plurality of activity categories. Each of the plurality of activity categories may further include a plurality of activities. The plurality of activity categories or activities may include, but are not limited to exercise, meditation, yoga, Pilates, martial arts, ikebana (flower arrangement), origami, painting, sculpting, pottery, physical rehabilitation, cooking, dancing, boxing, physical therapy and rehabilitation, Crossfit, Les Mills, F45, Zumba, Bikram Yoga, Orange Theory, or the like. The plurality of activity categories and subsequently activities may be presented on a Graphical User Interface (GUI) of the smart mirror 100. The user 102 may select one or more of the plurality of activities, which may then be presented to the user via the GUI as a multimedia content. As depicted in FIG. 1, the user 102 may have selected crunches as the desired activity, which is then presented to the user via the GUI as a multimedia content. The user 102 may then follow or imitate the steps as instructed in the multimedia content to perform crunches.

Figure 2:
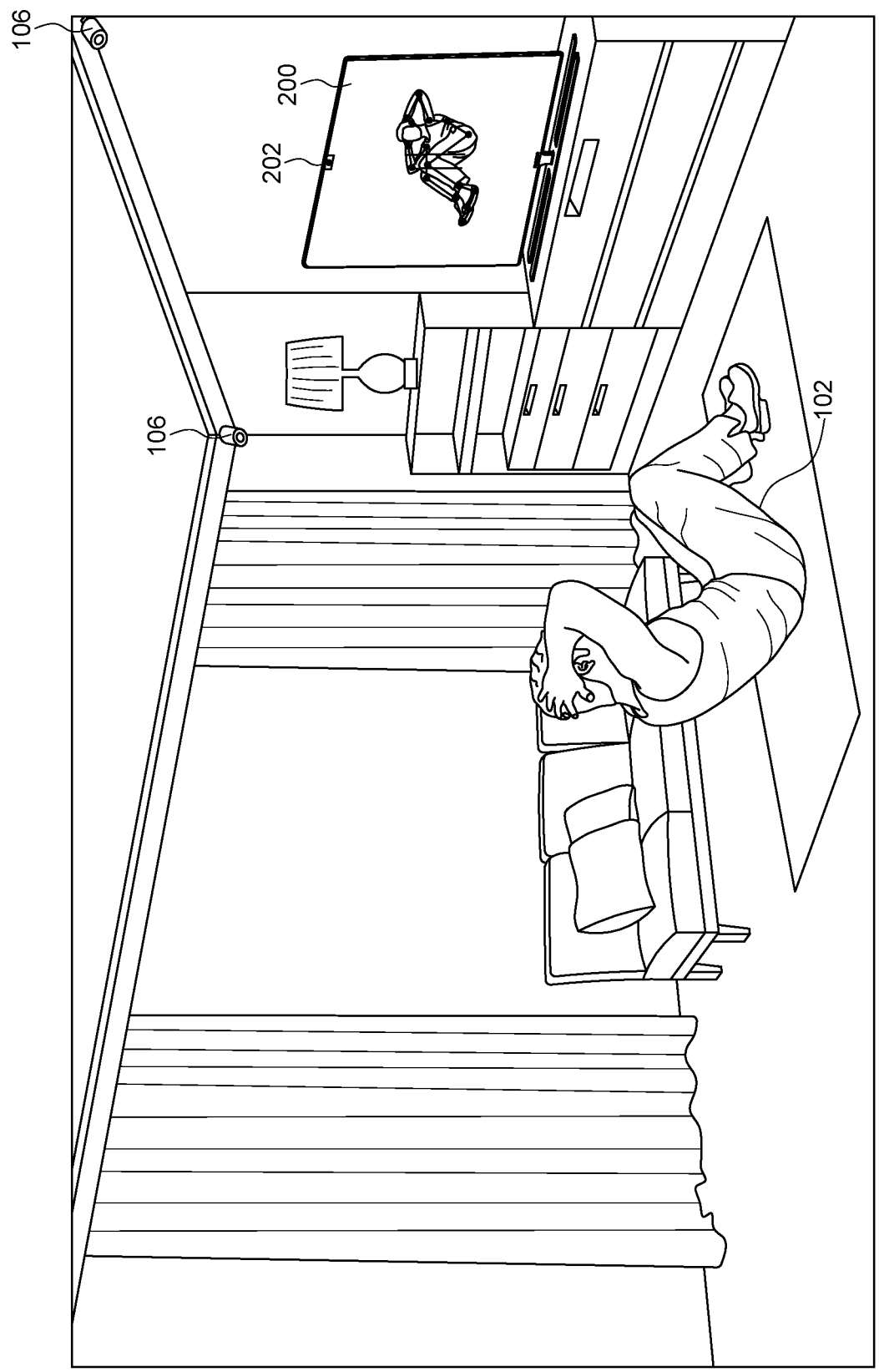
FIG. 2 illustrates an exemplary display device for providing AI assisted activity training, in accordance with some embodiments.

In a similar manner, instead of the smart mirror 100, as depicted in FIG. 2, a display device 200 that is configured to provide AI assisted activity training may be used. The display device 200 may also include the system that is configured to provide AI assisted activity training. The display device 200, for example, may be a smart TV, a mobile phone, a laptop, a tablet, or a smart projector with inbuilt camera. The display device 200 may include a display screen that may be used to present the user with the plurality of activity categories and subsequently one or more activities presented as multimedia content.

One of the differences between the smart mirror 100 and the display device 200 may be that the smart mirror 100 may augment or overlay information over a reflection of the user 102, while the display device 100 augments or overlays information over a video (live or recorded) of the user. Other than this difference, both the smart mirror 100 and the display device 200 perform similar functionalities in a similar manner. The smart mirror 100 and the display device 200 may include one or more cameras (a camera 104 and a camera 202 respectively), display screens, one or more processors (not shown), a memory (not shown), a microphone (not shown), one or more sensors (not shown), and a speaker (not shown). The one or more cameras, for example, may be infrared cameras, motion detection cameras, or the like. In addition to the inbuilt cameras 104 and 202, external cameras 106 may also be provided that may integrated with the smart mirror 100 and/or the display device 200. The external cameras 106 may enable capturing more information about the user 102 and the user environment. Examples of one or more sensors may include, but are not limited to Light Detection and Ranging (LiDAR), infrared sensor, motion sensor, proximity sensor, temperature sensors, or humidity sensors.

The display screen of the smart mirror 100 and the display device 200, for example, may include, but is not limited to a Liquid crystal display (LCD), a Light-emitting diode (LED) backlit LCD, a Thin-Film Transistor (TFT) LCD, an LED display, an Organic LED (OLED) display, an Active Matrix Organic LED (AMOLED) display, a Plasma Display Panel (PDP) display, a Quantum Dot LED (QLED) display, or the like.

The smart mirror 100 and the display device 200 may be operated or controlled by the user 102 using voice-based inputs. The voice-based input received from the user, via the microphone, may be processed by a Natural Language Processing (NLP) model configured within the smart mirror 100 and the display device 200. Examples of the NLP model may include, but are not limited to Bidirectional Encoder Representations from Transformers (BERT), Robustly Optimized BERT Pretraining Approach (RoBERTa), ALBERT XLNet, and the like.

The NLP model may process the voice-based inputs to extract user selection of one or more activities and the associated activity attributes. The NLP model may be configured using a single language and thus may also be called single language model. The single language, for example, may be English. Thus, when the user 102 provides a voice-based input in a source language (for example, Japanese), the NLP model first converts or translates the source language to an intermediate language that has been used to configure the NLP, which in this case is English. The NLP model may then process the voice-based input translated into the intermediate language, render the content as required or requested by the user, and may also render a feedback (if required) to the user in the source language only. In other words, the smart mirror 100 and the display device 200 are language agnostic and can be used by any user, anywhere in the world, irrespective of the language that they speak. Also, the NLP model ensures that no language based learning is required by the smart mirror 100 and the display device 200 before a user may start using these.

Additionally, the NLP model may be configured to correctly understand the user intent based on the context in which certain words and phrases (that may sound phonetically similar) are used. In other words, since the NLP model is configured based on context, it is able to clearly differentiate between utterance that may be potentially competing, based on the context in which they are used. By way of an example, the use of words "start" and "stop" for controlling a video based on voice commands is highly dependent on context. Moreover, since 'stop' and 'start' as single words may sound phonetically similar, understanding of the context by the NLP model to capture the correct intent is very important. The NLP model in the invention derives context from various sources including but not limited to, site section, user mode, such as, editing or activity workout, current pose, target pose, and progress of an activity. Additionally, it may be noted that the context is configured within the single language model.

It may be noted that in addition to and in combination with the voice-based inputs, the smart mirror 100 and the display device 200 may also be operated or controlled using one or more of, but not limited to touch gestures, air gestures, eye gestures, biometric inputs, game controllers, inputs via keyboard, mouse or any other input devices.

Also, to initiate or start using the smart mirror 100 and the display device 200 various security mechanisms may be used in order to ensure that an unauthorized user is not able to access the smart mirror 100 and the display device 200. Examples of such security mechanisms may include, but are not limited to alphanumeric password, pattern based passwords, voice recognition, biometric data (for example, retina scan, fingerprint, facial recognition, or heartbeat signature), One time Password (OTP), private key pairing, RFID tags, NFC tags, or proximity of a registered smart device.

The smart mirror 100 and the display device 200 may also connect and communicate with other computing devices (for example, a mobile phone, a laptop, a desktop, or a Personal Digital Assistants (PDA), and so forth), smart watches, fitness trackers, fitness bands, biometric sensors placed on a user, other smart mirrors and display devices over a communication network (for example, a cellular network, WiFi Bluetooth, internet, or the like). The smart mirror 100 and the display device 200 may also be communicatively coupled to a central server (not shown in FIGS. 1 and 2) over the communication network. In such case and in some embodiments, the system (which is the intelligence behind the smart mirror 100 and the display device 200) configured to provide AI assisted activity training may reside in the central server. Thus, in some embodiments, multiple smart mirrors 100 and/or display devices 200 may simultaneously present the same activity to respective users enabled by broadcast of the same recorded activity from the central server. This feature is helpful when a group training session may be planned by multiple users. This is further explained in detail in subsequent paragraphs.

In some alternate embodiments, the central server may broadcast a live training session conducted by a human trainer to multiple smart mirrors 100 and/or display devices 200 simultaneously. In context of description related to FIG. 1 and FIG. 2 and for ease of explanation, reference made to the smart mirror 100 hereinafter may also include the display device 200 and vice versa. It may further be noted that though various examples used to describe functionalities of the smart mirror 100 are related to different types of exercises, the invention is not limited to the same. Also, it will be apparent to a person skilled in the art that though examples have been depicted for a single user 102, a single smart mirror 100 or the display device 200 may be equipped to provide AI assisted activity training to multiple users at the same time.

As discussed before, when the user initiates or activates the smart mirror 100, the smart mirror 100 may present multiple activity categories as multimedia content. In an illustrative and non-limiting embodiment, the multiple activity categories may include, but are not limited to an 'all' activity category, an 'arms' activity category, a 'chest' activity category, a 'lunges' activity category, a 'legs' activity category, a 'quads' activity category, a 'shoulder' activity category, a 'squats' activity category and a 'triceps' activity category. Under the 'all' activity category, the presented multiple activities, for example, may include lateral squats, side lunges, side squats, side burpees, side push-ups, front overhead triceps, front push-ups, dumbbell squat press, front squats, and/or front lunges. Additionally, multiple activities included in each of the plurality of activity categories may also be presented on the GUI of the smart mirror 100, based on user selection of an activity category.

Based on the presented multimedia content, the user 102 may select an activity or an activity training plan through a voice-based input in a source language. It may be noted that user input may also be received via touch gestures, air gestures, eye gestures, biometric inputs, game controllers, inputs via keyboard, mouse or any other input devices. By way of an example, the activity training plan may include selection of lateral squat activity and side push-ups activity from the 'all' activity category, and one or more other activities from the 'squat' and the 'lunges' activity categories. Using the voice-based input, the user 102 may additionally select an activity attribute associated with each of the one or more selected activities. Activity attributes may include, but are not limited to one or more of sequence of execution of the one or more selected activities, the number of sets for performing each of the one or more selected activities, a count for each of the one or more selected activities in each of the sets, duration of performing each of the one or more selected activities, rest period between each of the sets, intensity of performing each of the one or more selected activities, difficulty level of performing each of the one or more selected activities, or pace of performing each of the one or more selected activities. With regards to difficulty level, the user 102, for example, may have an option to select between a beginner level or an advanced level.

Once the user 102 has selected the one or more activities and the one or more associated activity attributes, a multimedia content in accordance user selection may be presented to the user 102 via the GUI of the smart mirror 100. The multimedia content may include multiple guidance steps for the one or more activities that may be performed by a virtual assistant. The virtual assistant, for example, may be an avatar (3D or 2D) of a trainer or an expert who performs multiple guidance steps involved in a given activity. The guidance steps may include instructions related to correct posture, pose, and/or pace of performing an activity. By way of an example, when the activity is front squats, the guidance steps or instructions may include maintaining space between feet, bending position and angle of knees with respect to feet, and depth of the squat, placement of hands, correct orientation of a dumbbell or kettle bell, and/or angle of inclination of the back.

Once the user 102 initiates user activity performance, one or more cameras configured with the smart mirror 100 may detect initiation of the user activity performance. The detected user activity performance may include performance of a series of steps of the activity by the user 102 in response to the presented guidance steps. The one or more cameras (that may be placed at distributed locations) may also capture a video of the user activity performance. In an embodiment, during the user activity performance, the smart mirror 100 may overlay a pose skeletal model corresponding to the user activity performance over a reflection of the user on the smart mirror 100, while performing the activity. This may provide the user 102 with a real-time feedback as to the performance of the user 102 with regards to the given activity. The smart mirror 100 may also overlay a pose of the user over a video stream of an instructor or over the guidance steps of the virtual assistant performed during the training.

For providing the AI assisted activity training, the smart mirror 100 may use an AI model to process the video of the user activity performance captured by the one or more cameras to extract a set of user performance parameters. In general, the AI model may process the video to determine the posture, the pose, and the body movements of the user 102. In addition to the one or more cameras, motion and/or biometrics parameters of the user 102 may be determined using one or more sensors, which may be configured with the smart mirror 100 or may be worn by the user 102. Examples of the sensors configured with the smart mirror 100 may include LiDAR, infrared, motion sensors, proximity sensors, or temperature sensors. The AI model, in addition to processing the captured video, may also process data captured by one or more of these sensors. In some configurations, the one or more sensors may be part of various health monitoring devices (for example, fitness bands, smart watches, and other similar smart wearables) worn by the user 102. The information captured by the one or more sensors may be used to determine various biometric parameters of the user 102 during the user activity performance. The biometric parameters may also be a part of the user performance parameters. The user performance parameters may also be received from smart weights and strength bars used by the user 102. To this end, the smart mirror 100 may be configured with appropriate programming and communication interfaces to couple with such external smart devices.

In some configurations, the AI model may further include different portions of AI models, each of which is configured to perform distinct functionalities. For example, one AI model may be configured for pose matching, while other AI model may be configured for key point (or skeletal point) recognition. In such case, the AI model configured for pose matching may reside on a remote server, while the AI model configured for key point recognition may reside on an edge device, for example, the smart mirror 100. As a result of assigning such distinct functionalities to different AI models, the requirement of transferring heavy data (for example, video data) to the remote server may not be required. This distinction between AI model is also done for enhanced data security, as it is safer to perform pose recognition and matching at the remote server than an edge device (for example, the smart mirror 100) which is shared by multiple people.

The user performance parameters may include, but are not limited to speed of a current activity performance, number of repetitions completed, overall completion of an activity circuit, third-party smart device information, pulse/heart rate of the user 102, heart beat pattern of the user 102, blood pressure of the user 102, calories burnt by the user 102, Electrocardiogram (ECG) parameters, level of perspiration of the user 102, and motion of the user 102.

Once the set of user performance parameters have been extracted, the AI model may compare the set of user performance parameters with a set of target performance parameters. In a manner similar to the set of user performance parameters, the set of target activity performance parameters may include, but are not limited to speed of the target activity performance, blood pressure, target number of repetitions, target pulse rate of the user, and target motion of the user. Upon observing a difference or deviation between the two set of parameters (i.e., user vs target), the AI model may generate a feedback for the user.

The feedback may be instantly provided in real-time or contemporaneous to the user 102 performing a given activity. To ensure that correct and timely feedback is generated and shared, a tight coupling of the user movement may be done with available performance guidance clues, target movements, media and voice and audio feedback. Additionally or alternatively, the feedback may be provided after the user has completed the given activity. The feedback may include, but is not limited to one or more of the amount of calories burnt, maximum count of an activity performed, maximum time spent on the activity during a previous activity session of the user 102, incorrect posture or pace of the user 102 while performing the activity, correct posture or pace to perform the activity, absolute activity performance proficiency of the user 102, relative activity performance proficiency of the user 102, best time taken to perform the activity, or warnings associated with biometric parameters of the user 102.

The feedback may then be rendered to the user 102 in any of an aural form, a visual form, or as a haptic feedback. The visual form may include text in combination with various graphics displayed via the GUI. By way of an example, the feedback may correspond to adjusting the pose, movement pattern, and speed of the activity of the user 102 to match an expected pose, movement pattern, and speed that may correspond to an instructor or an expert.

While aural or audio feedback may be audio instructions shared with the user 102 via the speakers of the smart mirror 100 or headphones/earphones worn by the user 102. The instructions may be related to a corrective action with regards to posture, pace, or movement pattern that may be taken by the user 102 in order to perform a given activity properly. By way of an example, instructions to the user 102 while he is doing "barbell curls" may be "adjust elbows to a lower position," "fix elbow position," "don't move elbow while curling," and/or "release barbell slowly." By way of another example, instructions to the user 102 while he is doing "front squats" may be "increase/decrease distance between feet," "keep knees at 90 degree to the floor," "lower the hips and bring to knee level" and/or "keep your core engaged." The audio feedback may also include rhythm audio cues, such as a metronome, which may be used to guide the user as to repetitions of an activity or pace of performing an activity.

The visual feedback may include the same instructions that are displayed to the user 102 via the GUI of the smart mirror 100. Thus, the visual feedback, for example, may include instructions in textual form that may be displayed on the smart mirror 100 along with various graphic elements. It may be noted that the graphic elements may include both static elements and dynamic elements that may include motion based graphics. For example, directional arrows rendered on the GUI of the smart mirror 100 may be used along with textual instructions to indicate to the user 102 that his elbows need to be lowered while performing barbell curls or the user 102 needs to keep his back upright while doing front squats. Additional graphic elements, such as, graphic indices, animations, highlights, or bright or dark regions, colored symbols may also be used to provide the feedback.

In some embodiment, the visual feedback may be in the form of skeletal pose model or skeletal points overlayed on the reflection of the user 102 in the smart mirror 100. The skeletal points may be overlayed on corresponding joints of the user 102, for example, knees, hip joint, elbows, wrists, feet, and other joints. Whenever the user 102 is performing an activity using wrong pose or movement, one or more of these skeletal points may be activated or highlighted to indicate the same to the user 102 instantly. In case of the display device 200, the skeletal pose model or the skeletal points may be overlayed on a video stream captured for the user 102 while performing the activity. In some other embodiments, a multidimensional (3D or 2D) model of the user 102 or the virtual assistant may also be displayed via the GUI to provide feedback to the user.

In some cases, the multidimensional model may be overlayed on the reflection of the user 102 or the video of the user 102 while performing a given activity. The tight coupling discussed above plays an important role in ensuring that the skeletal pose model, skeletal points, or multidimensional avatars are correctly and timely overlayed. With regards to visual feedback, the feedback may also be provided as additional video clips, as inserted video clips incorporated into the instructor's video that includes an instructor providing specific feedback, and instructions for the user 102. The system 100 may map and synchronize multimedia content and information as provided with actual movement of the user 102 and may thus provide relevant corresponding feedback.

With regards to the haptic feedback, the user 102 may have haptic devices or interfaces placed on specific body parts (joints or muscles) of the user 102. The haptic feedback may be used to provide an experience of touch by applying forces, vibrations, or motions to the user 102. In this case, the feedback may be generated in the form of specific vibrations or application of forces to specific body parts of the user in order to indicate that the user 102 is not performing the activity properly. For example, for a wrong elbow or knee position, haptic devices placed on these body parts may be activated to generate a vibration or force. In some embodiments, specific vibration patterns may be predefined to indicate whether the issue is with motion, pose, or movement pattern. In some other embodiments, one type of vibration (longer duration) may indicate incorrect performance, while other type of vibration (short duration in bursts) may indicate correct performance. A sequence of haptic feedbacks may also be used to instruct or guide the user 102 to gradually correct his posture, pace, and/or movement pattern.

As may be appreciated, the feedback based on the activity being performed by the user 102 may not be limited to instructions to perform corrective actions. The feedback may also include biometric feedback or warnings, for example, any irregularity or issues in one or more of pulse rate or heartbeat of the user 102, body temperature of the user 102, spasms in muscles, pupil dilation, and other similar health issues.

In some embodiments, feedback may be in the form of motivation or encouragement provided to the user 102 while performing the activity or after completion of the activity. By way of an example, in the form of audio feedback, messages like: "great job," "you are awesome," "great going," "perfectly done," "done like a pro," "you are the best," "that's the best I have seen," and other similar messages, may be provided to the user 102. The sound of clapping, cheers, or various exclamations may also be provided to the user 102 as feedback. These messages may also be provided in the form of visual feedback, such that, the messages may be displayed in textual form on the GUI of the smart mirror 100. Additionally, or alternatively, graphic elements, for example, bursting crackers, flying balloons, sound of stadium crowd, or avatars of cheer leader, instructor, famous people (for example, Kai Greene, Phil Health, Ronnie Coleman, Arnold, or other know personalities), may also be displayed to the user 102. In some configurations, gamification of the activities performed by the user and a rewarding mechanism may also be used as feedback provided to the user. As a result of such feedback, the user 102 may be constantly motivated and may not feel that he/she is performing any given activity in silo.

In some configurations, the user 102 may also be able to set goals related to various activities. In such case, the feedback may include status regarding percentage of goals achieved by the user 102.

In some embodiments, in order to provide feedback to the user 102 on their personal smart devices, i.e., third party smart devices, the smart mirror 100 may be configured with an open Application Programming Interface (API), which may enable such integration seamlessly. Moreover, data received from the third party smart devices may also be ingested into the smart mirror 100, via the open API, and may further be provided to the user 102 via the smart mirror 100 using visual elements (such as, graphs or charts), verbal and audio cues, or haptic cues. The data may also correspond to warnings and alerts generated by the third party smart devices. By way of an example, a smart watch that is configured to sense blood pressure of the user 102 may send data regarding the user 102 having high blood pressure to the smart mirror 100. Accordingly, the smart mirror 100 may render the message "Your blood pressure is too high, please relax and take a break" to the user 102, orally or visually. Thus, the smart mirror 100 may act as a collator of feedback and a single point smart device for viewing all feedbacks. In other words, since the smart mirror 100 generates feedback on its own and also receives feedback from other smart devices, the smart mirror 100 assimilates all feedback, refines it, and the presents it to the user 102 via the smart mirror. Thus, the user does not have to rely on multiple devices to receive various types of feedbacks.

Further, the user 102 may want to share activity performance with his friends on various social networks or with other remote users that may also use smart mirrors 100. To this end, the smart mirror 100 may be configured with various integrate with social media applications. Examples of these social media applications may include, but are not limited to FACEBOOK™, WHATSAPP™, YOUTUBE™, and/or INSTAGRAM™. In some embodiments, the smart mirror 100 may have these social media applications already installed therein. There may also be a social media application that is specific to the smart mirror 100 and is configured to only connect users of other smart mirrors 100 and/or display devices 200.

Thus, by way of integration with these social media applications, the user performance may be posted and published on one or more of these social media platforms and may be made available as online content for other users to access. The rewarding mechanism as discussed before may also be shared or used on social media platforms. In some configurations, scores related to user activities may be presented on a leader board as points for various users who use smart mirrors 100 and/or display devices 200. Badges or medals may also be assigned to various users based on level, quantity, or quality of activities performed by them and may be displayed on social media platforms. Additionally, records related to exercises performed may also be displayed.

Moreover, goals set by various users for activities and respective percentage completion of goals may also be displayed on social media platforms. As may be appreciated, feedback provided to users may also be shared within group of users on social media, including friends, social circles, and classes that may be connected in real-time. Further, in an embodiment, when the user 102 is performing an activity, content media related to the activity performance may be created and shared with one or more users via social medial applications. The content media may also be augmented with information that may include, but is not limited to current health status of the user, exercising routine, exercising capacity, previous records, and rewards earned by the user on various social media platforms.

As mentioned before, instead of having a virtual assistant provide instructions and guidance steps for performing various activities, a real trainer or instructor may provide instructions and guidance steps. The instructor, for example, may be personal coaches, trainers, gym instructors, physical therapist, occupational therapist, physical education teachers, martial arts teachers, dance and choreography teachers, sports personalities, team coach, demonstrators and other trainers in health and fitness. In case such instructions are provided live, the real trainer or instructor may be located at a place where his/her video is recorded and broadcasted live to multiple smart mirrors 100 at the same time. As is the case with the virtual assistant, in case of the live broadcast as well, the instructions for performing the activity and respective feedback generated may be displayed on the smart mirror 100. Further, similar instructions and feedback may also be generated by the instructor for other users using a different smart mirror 100 or display device 200. In some embodiment, a user using the smart mirror 100 may share instructions and the feedback received from the instructor with one or more users present at remote locations, who are using their respective devices.

Figure 3A:
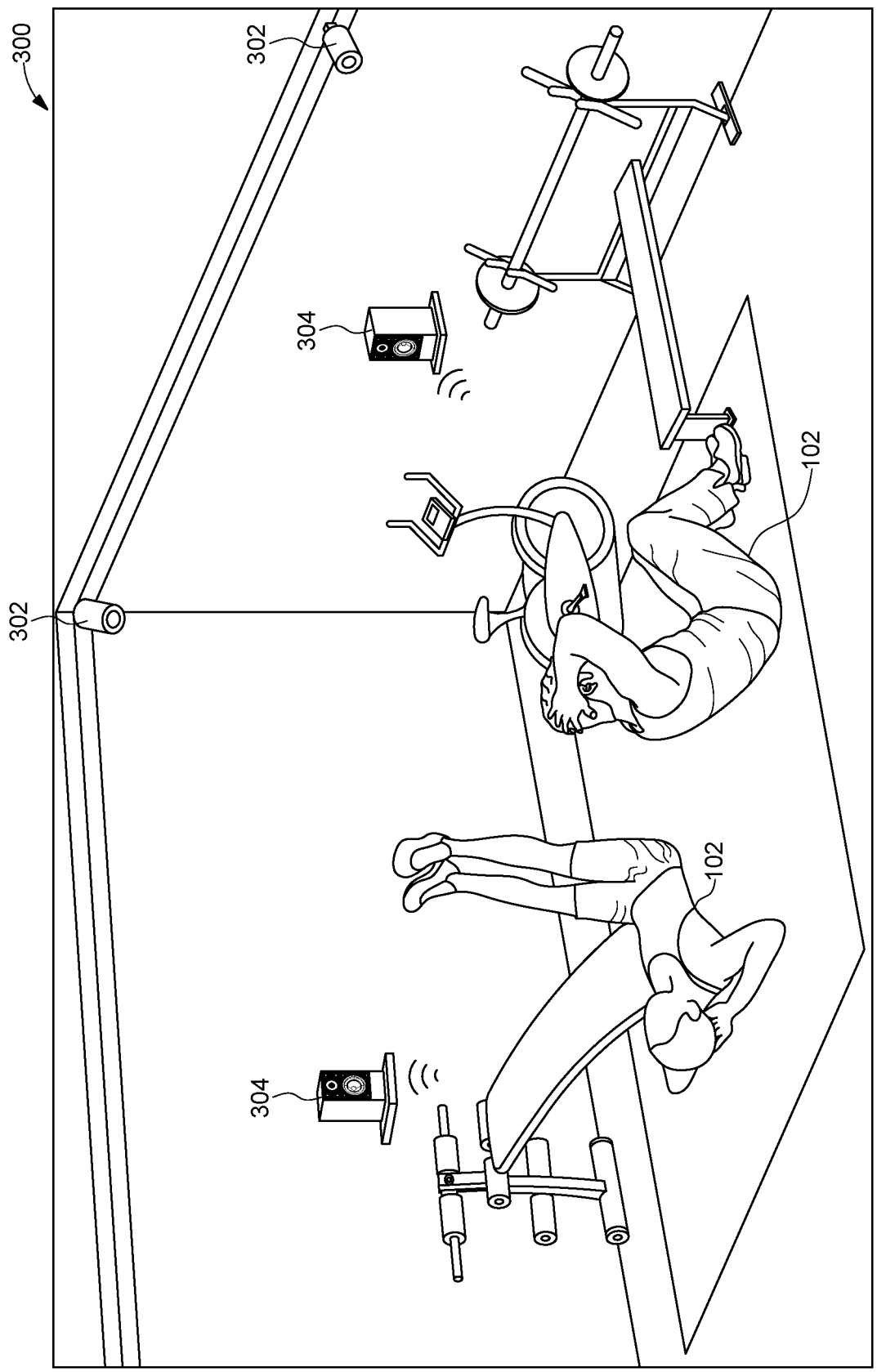
FIGS. 3A and 3B illustrate providing the AI assisted activity training in a gymnasium, in accordance with some embodiments.
Figure 3B:
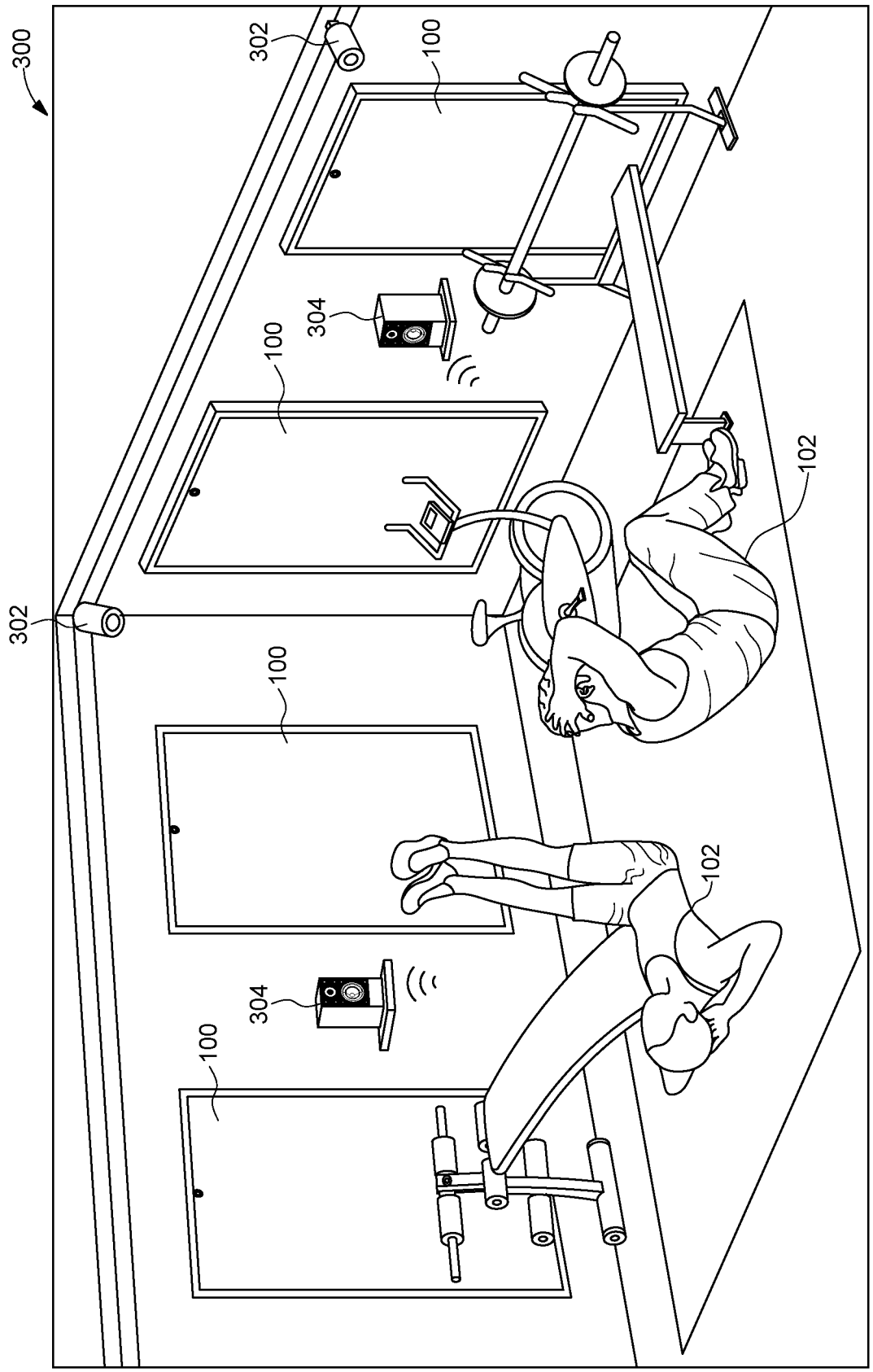

Referring now to FIGS. 3A and 3B, providing the AI assisted activity training in a gymnasium 300 is illustrated, in accordance with some embodiments. As illustrated, multiple users (for example, users 102) may be present in the gymnasium 300 and each of the multiple users may be performing similar or different activities. As depicted, the gymnasium 300 may have multiple exercise machines and equipment for performing multiple activities by the users. The gymnasium 300 may have multiple cameras 302 installed at distributed locations withing the gymnasium 300, that are communicatively coupled to a central server that includes a system that is configured to provide AI assisted activity training. The system is the same as mentioned in FIGS. 1 and 2 that powers the smart mirror 100 and the display device 200. The system is further explained in detail in conjunction with FIG. 4.

The central server may either be located within the gymnasium 300 or may be located at a remote location. In some embodiments, the smart mirror 100 and/or the display device 200 may not be used. In such embodiments, the users may have headphones that may automatically get connected to the central server the moment the users enter. Alternatively or additionally, directional speakers 304 may be installed in the gymnasium 300, which may send out directional sound beams to specific and targeted users. Additionally, the cameras 302 may identify and recognize each of the user using facial recognition techniques. The users, is some scenarios, may have a mobile application installed on their mobile devices, such that, the mobile application may be connected with the central server. In this case, the moment a user enters the gymnasium 300 and open the mobile application, the user's presence in the gymnasium 300 is identified.

Irrespective of the methodology used to connect with the central server within the gymnasium 300, the cameras 302 may capture activity of the users, which may then be processed by the system installed at the central server. Accordingly, the system may provide relevant instructions and feedback to the users for improving the activities being performed. This has already been discussed in detail in conjunction with FIG. 1 and FIG. 2. It may be noted that the cameras 302 may also track and record the activity of the users in the gymnasium 300 as the users moves from one area to other or from one machine to another for performing various activities. The cameras 302 may allow continuity of the user's context and information across various areas within the gymnasium 300. It may further be noted that in some embodiments one or more smart mirrors 100 and display device 200 may also be placed within the gymnasium 300. This is depicted in FIG. 3B. In this configuration for the smart mirrors 100, there may be one contiguous smart mirror 100 of a large size and there may be multiple displays behind the contiguous smart mirror 100. Thus, multiple users may be able to use the single smart mirror 100 at the same time. Thus, in such embodiments, the users can work out within the gymnasium 300 without availing services of personal trainers or instructors, and still get continuous feedback as to improvements and corrective action to be performed for any given activity.

Figure 4:
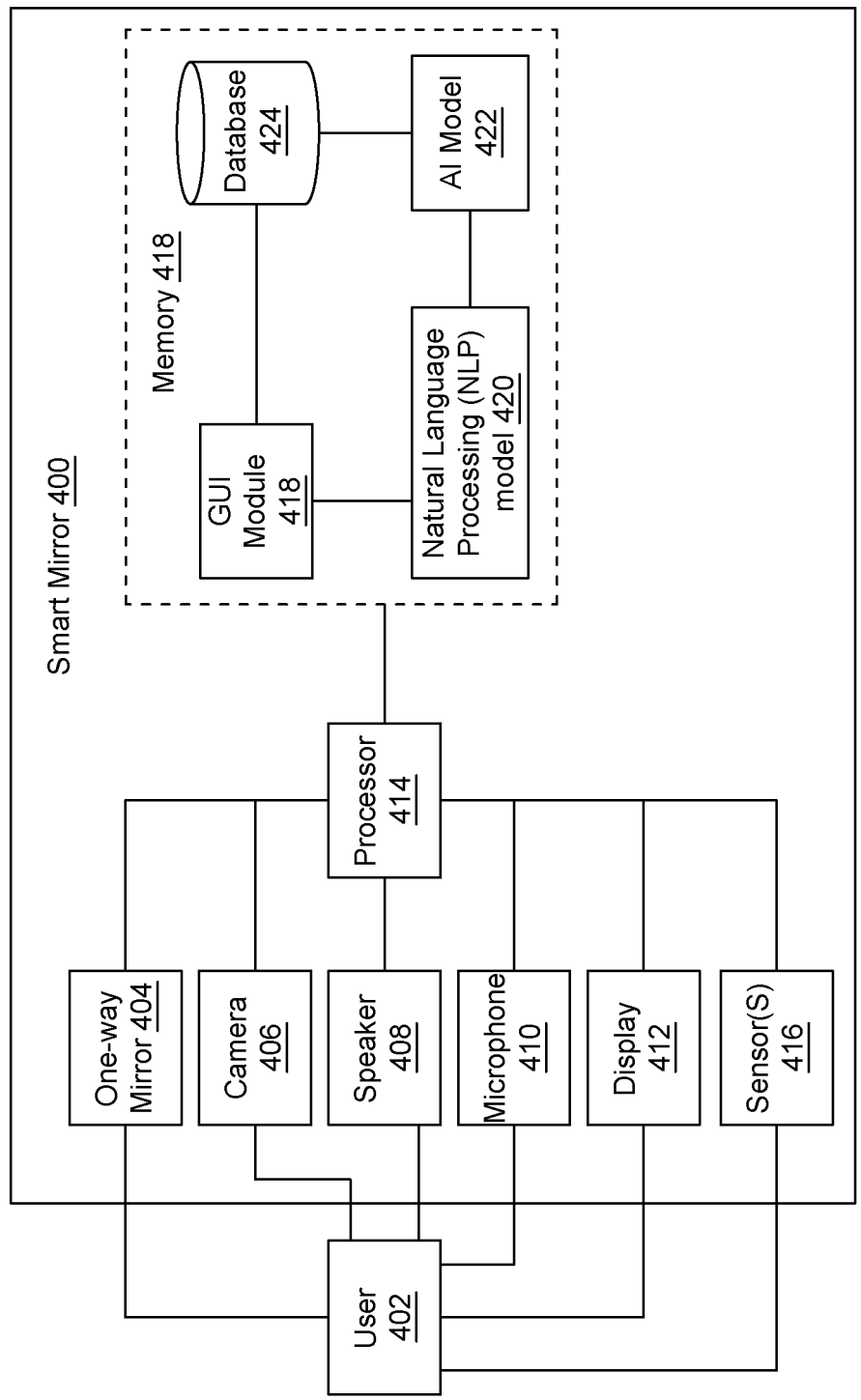
FIG. 4 illustrates a functional block diagram of an exemplary system for providing AI assisted activity training, in accordance with some embodiments.

Referring now to FIG. 4, a functional block diagram of a system 400 for providing AI assisted activity training to a user 402 is illustrated, in accordance with some embodiments. The system 400 may include a one-way mirror 404, a camera 406, a speaker 408, a microphone 410, a display 412, a processor 414, one or more sensors 416, and a memory 418. The memory 418 further includes a Graphical User Interface (GUI) module 426, a Natural Language Processing (NLP) model 420, an AI model 422, and a database 424. As will be appreciated, the system 400 may not include the one-way mirror 404, when the system 400 is supporting or powering display devices 200.

In configurations for the smart mirror 100, the display 412 may be coupled with the one-way mirror 404, such that, the one-way mirror 404 may covers the display 412. Further, the one-way mirror 404 may be configured to partially reflect an image of the user 402 and partially show the display 412 to the user 402. Therefore, the one-way mirror 404 may act as a semi-reflective surface for the user 402 and may act as a semi-transparent surface for the display 412. The display 412 may be of same dimensions as the one-way mirror 404. In an embodiment, the one-way mirror 404 may be of a size of a dressing table mirror, a full length mirror, or the size of a television. As discussed before, in configurations for the display device 200, the display 412 may be directly viewable by the user 402.

The GUI module 426 may be accessible to the user 402 via the display 412. The GUI module 426 may provide a plurality of activity categories to the user 102. By way of an example, the plurality of activity categories may include, but may not be limited to exercise, meditation, yoga, Pilates, martial arts, ikebana (flower arrangement), origami, painting, sculpting, pottery, cooking, dance, boxing, physical therapy and rehabilitation, Crossfit, Les Mills, F45, Zumba, Bikram Yoga, Orange Theory, or the like. Each of the plurality activity categories may further include a plurality of activities. In order to select an activity category from the plurality of activity categories and subsequently one or more activities from the plurality of activities associated with the activity category, the user 402 may provide voice-based inputs via the microphone 410. Alternatively or additionally, the user 402 may provide inputs via a touch gesture, an air gesture, an eye gesture, a biometric data input, or a signal generated by an input device (for example, a mouse, a touch pad, a stylus, a keyboard, or the like).

The voice-based input (or any other form of user input) may further include an activity attribute that is associated with each of the one or more activities. It may be note that the user 402 may generate the voice-based input in a source language. On receiving the voice-based input in the source language, the NLP model 420 may process the received voice-based input to extract the selection of the one or more activities and the one or more associated activity attributes. Examples of the NLP model 420 may include, but are not limited to Bidirectional Encoder Representations from Transformers (BERT), Robustly Optimized BERT Pretraining Approach (RoBERTa), ALBERT XLNet, and the like). The NLP model 420 may be configured using a single language. The single language, for example, may be English. Thus, when the user 402 provides a voice-based input in a source language (for example, Japanese), the NLP model 420 first converts or translates the source language to an intermediate language that has been used to configure the NLP, which in this case is English. The NLP model 420 may then process the voice-based input translated into the intermediate language, render the content as required or requested by the user 402, and may also render a feedback (if required) to the user 402 in the source language only.

Based on the voice-input (or any other form of user input for that matter) received from the user 402, the display 412 may initiate presentation of a multimedia content. The presented multimedia content may be in conformance with the one or more activities and the one or more associated activity attributes. The multimedia content may include a plurality of guidance steps performed by a virtual assistant corresponding to the one or more activities. This has already been explained in detail in conjunction with FIGS. 1 and 2. Upon initiation of presentation of the multimedia content, the camera 406 may detect in real-time, initiation of user activity performance of the user 402 and may subsequently capture a video of the user activity performance.

The AI model 422, in real-time, may then process the captured video to extract a set of user performance parameters of the user 102 based on the user activity performance. Further, the AI model 422 may generate a feedback based on differential between the set of user performance parameters and a target set of performance parameters. The feedback may then be rendered to the user in one or more of an aural form, a visual form, or as a haptic feedback. The feedback may include, but is not limited to amount of calories burnt, maximum count of the at least one activity performed, maximum time spent for the at least one activity during a previous activity session of the user, incorrect posture or pace of the user while performing the at least one activity, correct posture or pace to perform the at least one activity, absolute activity performance proficiency of the user, relative activity performance proficiency of the user, best time taken to perform the at least one activity, or warnings associated with biometric parameters of the user. The feedback may also include content related to user encouragement and motivation. It may be noted that feedback in the aural form may be rendered to the user 402 via the speaker 408 and feedback in the aural form may be rendered to the user 402 via the display 412. Lastly, the haptic feedback may be rendered to the user 402 via haptic devices placed on the user 402. This has already been explained in detail in conjunction with FIGS. 1 and 2

In order to generate an exhaustive feedback, the user activity performance may also be measured by the sensors 416, which may be placed on the user 402. The sensors 416 may also be a part of various health or fitness monitoring devices that are worn by the user 402. The sensors 416, for example, may include, but are not limited to 3 axis accelerometer, gyroscope, motion sensor, pedometer, temperature sensor, pulse sensor, proximity sensors, or SPO2. This has already been explained in detail in conjunction with FIGS. 1 and 2

It should be noted that all such aforementioned modules 404-424 may be represented as a single module or a combination of different modules. Further, as will be appreciated by those skilled in the art, each of the modules 404-424 may reside, in whole or in parts, on one device or multiple devices in communication with each other. In some embodiments, each of the modules 404-424 may be implemented as dedicated hardware circuit comprising custom application-specific integrated circuit (ASIC) or gate arrays, off-the-shelf semiconductors such as logic chips, transistors, or other discrete components. Each of the modules 404-424 may also be implemented in a programmable hardware device such as a field programmable gate array (FPGA), programmable array logic, programmable logic device, and so forth. Alternatively, each of the modules 404-424 may be implemented in software for execution by various types of processors (e.g., processor 414). An identified module of executable code may, for instance, include one or more physical or logical blocks of computer instructions, which may, for instance, be organized as an object, procedure, function, or other construct. Nevertheless, the executables of an identified module or component need not be physically located together, but may include disparate instructions stored in different locations which, when joined logically together, include the module and achieve the stated purpose of the module. Indeed, a module of executable code could be a single instruction, or many instructions, and may even be distributed over several different code segments, among different applications, and across several memory devices.

Figure 5:
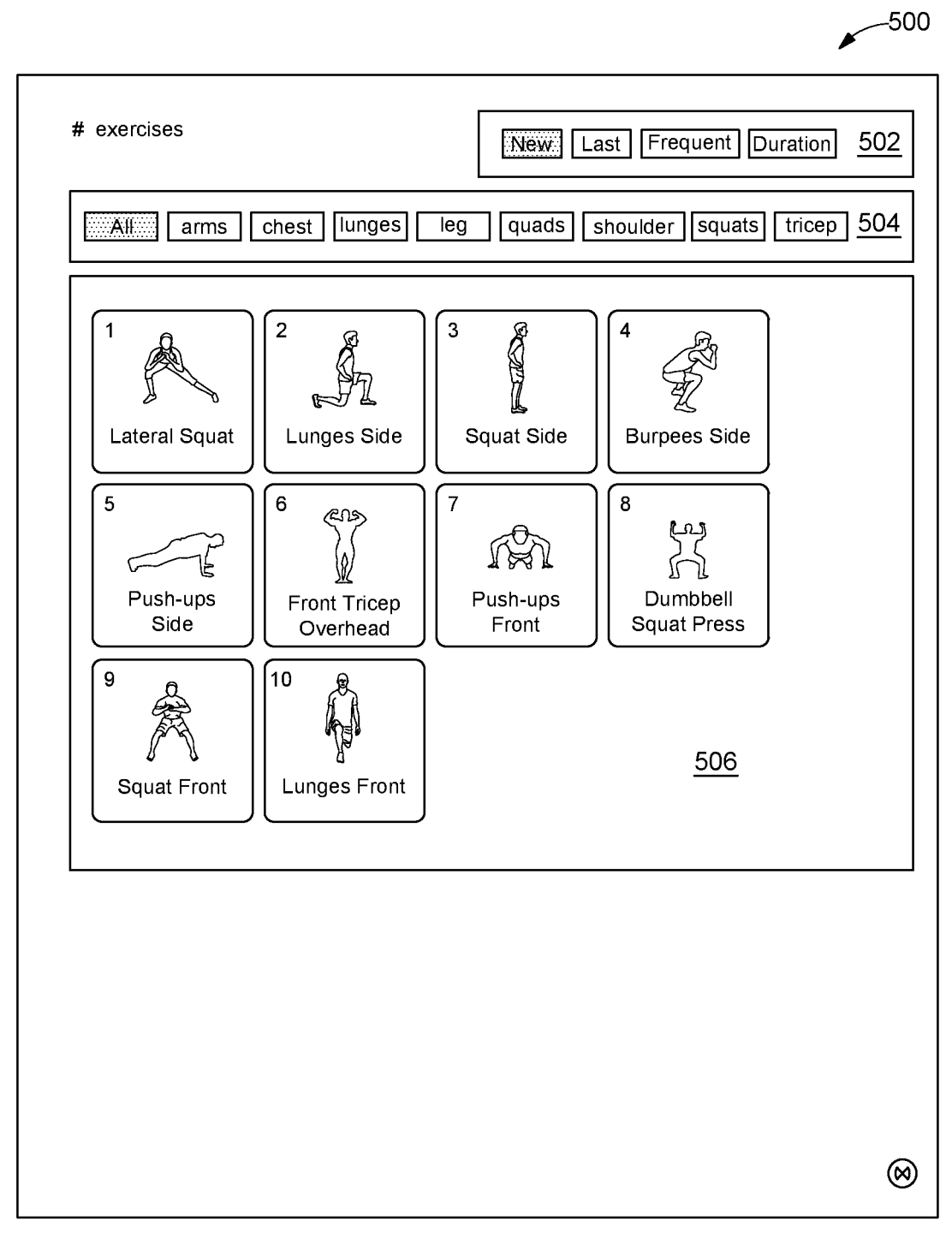

With reference to FIG. 5, a GUI 500 of a plurality of activity categories for AI assisted activity training is illustrated, in accordance with some exemplary embodiments. With respect to FIG. 5, a set of activities based on specific timeframes are presented on a GUI 500 of the smart mirror 100. At 502, multiple options are presented to the user 102, which may include, but are not limited to a new of set activity categories, the last set of activity categories performed by the user 102, activity categories that have been frequently accessed by the user 102, and exercises sorted based on a specific durations of use may be presented on the GUI 500.

At 504, a set of activity categories are presented, which may include an 'all' activity category, an 'abs' category, an 'arms' category, a 'back' category, a 'chest' category, a 'glutes' category, a 'legs' category, a 'punch' category, a 'quads' category, a 'shoulder' category, a 'squats' category, and a 'triceps' category. As discussed before, each of the activity categories may further include a plurality of activities.

At 506, the plurality of activities under one or more activity categories is presented. By way of an example, the 'abs' category may the following activities: core scissors and elbow knee; the 'arms' category may include the following activities: a band lateral raise, a band lateral side stretch, a front hook, a front uppercut, side boxing; the 'back' category may include the following activities: a front kettlebell, side deadlift a dead bug, and squat thrusters; the 'chest' category may include the following activities: side burpees, side push-ups, and front push-ups; and the 'glutes' category may include the following activities: lateral squat, side squat, side burpees, a dumbbell squat press, and a front squat.

Further, the 'legs' category may include the following activities: standing hip extension, standing hip flexion, hip abduction, quick feet abduction, bird dog, cross behind lunge, front kettlebell, side deadlift, dead bug, squat thrusters, drop squat, and front lunges; the 'punch' category may include the following activities: front hook, front uppercut, and a side boxing activity; the 'quads' category may include the following activities: lateral squat, side squat, side burpees, dumbbell squat press, and front squat; the 'shoulder' category may include the following activities: shoulder dislocates, band lateral raise, band lateral side stretch, front hook, front uppercut, side boxing, side lunges, side burpees, front push-ups, and dumbbell squat press; the 'squats' category may include the following activities: lateral squat, side squat, side burpees, and front squat; and the 'triceps' category may include the following activities: front triceps overhead, front triceps sitting, and front triceps sitting.

As depicted in the GUI 500, the user 102 may have selected the 'All' activity category based on voice-based user input or any other type of user input as explained in the description above. Thus, based on the user selection of the 'All' activity category, a mix of various activities may be presented to the user 102 via the GUI 500. The user may then select one or more of these activities and may also provide activity attributes for each of the one or more activities. This is further explained in conjunction with FIG. 6.

In some configurations, the user 102 may also create a new activity category and one or more new activities. The new activity category and the one or more new activities may either be downloaded from a remote server or may be recorded by the user 102 himself/herself using the camera of the smart mirror 100. The new activity category and the one or more new activities may then get added to the GUI 500.

Figure 6:
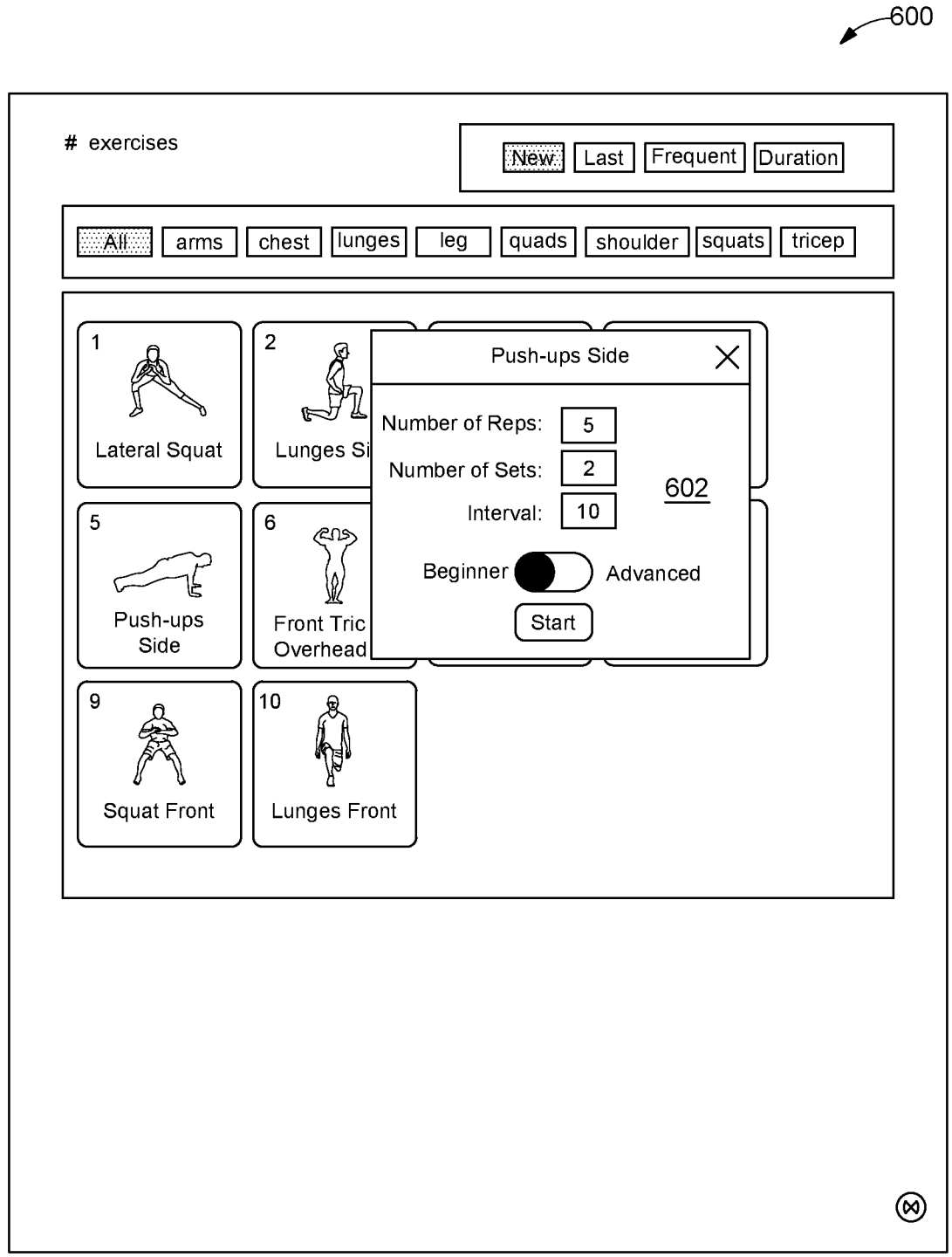
FIG. 6 illustrates a GUI depicting selection of an activity and corresponding activity attributes for the selected activity in response to a user input, in accordance with some exemplary embodiments.

With reference to FIG. 6, a GUI 600 for selection of an activity and corresponding activity attributes for the selected activity in response to a user input is illustrated, in accordance with some exemplary embodiments. The user 102 may select an activity training plan from the plurality of activity categories. For example, the user 102 may generate a voice-based command saying: "select arms" in order to select the 'arms' activity category and may subsequently say "select a band lateral raise" and then say "select a band lateral side stretch" in order to select some activities listed within the 'arms' category. Thereafter, the user 102 may provide activity attributes for each of the activities selected by the user 102. As explained before, the one or more of activity attributes may include, but are not limited to sequence of execution of the activity, a number of sets for performing each of the activity, a count for each of the activity in each of the sets, duration of performing each of the activity, rest period between each of the sets, intensity of performing each of the activity, difficulty level of performing each of the activity, or pace of performing each of the activity. Additionally, activity attributes may also include level of expertise for performing an activity. The level of expertise to be selected by the user 102, for example, may include a beginner level, an intermediate level, or an advanced level.

With reference to FIG. 5 and in further continuation, as depicted in the GUI 600, once the user 102 has selected the 'All' activity category, the user 102 may further select the side push-ups activity. Thereafter, as depicted, the user 102 may also define activity attributes for the side push-ups activity in an activity attribute section 602 as: "Number of Reps =5," "number of sets =2", "interval =10 seconds," and expertise level as "Beginner." Once the user 102 has provide the activity attributes, the user 102 may activate the start button in the activity attribute section 602 and the activity may be presented as a multimedia content to the user 102 in conformance with the activity attributes defined by the user. This is further explained in conjunction with FIG. 7.

Figure 7:
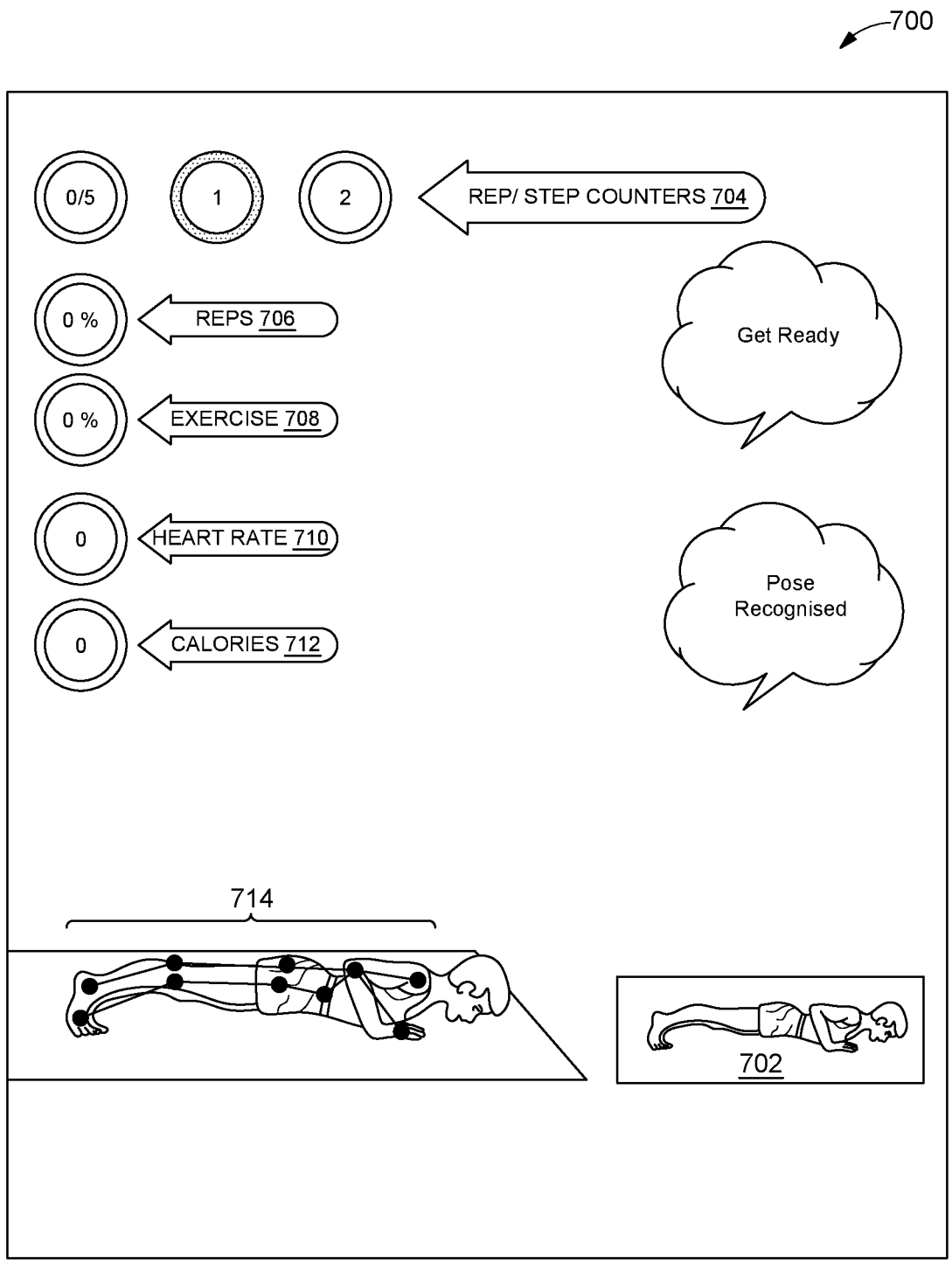
FIG. 7 illustrates a GUI depicting initiation and monitoring of user activity performance in response to presentation of guidance steps associated with an activity, in accordance with some exemplary embodiments.

Referring now to FIG. 7, a GUI 700 depicting initiation and monitoring of user activity performance in response to presentation of guidance steps associated with an activity is illustrated, in accordance with some embodiments. With reference to FIG. 6, once the user 102 has selected the side push-ups activity and provided the activity attributes via activity attribute section 602, the user 102 may be presented with a plurality of guidance steps (as multimedia content) performed by a virtual assistant 702. The plurality of guidance steps may guide the user 102 to properly perform the side push-ups activity.

Before initiating the plurality of guidance steps, the virtual assistant 702 may instruct the user 102 via a video and/or aural message to "get ready." The user 102 may then take an initial pose for initiating the activity. Voice-based instructions become essentially important when the user 102 is setting up the initial pose, since the user 102 may not be able interact with the GUI of the smart mirror by way of touch or any other input means to start the activity. For example, while holding an elastic band in a certain way or while holding weights, the user 102 may not be able to physically interact with the smart mirror 100 and voice-based instruction are the most effective way to interact. A video/reflection of the user 102 overlayed with a 3D model of the user/trainer, a skeletal pose model 714, or skeletal points may be provided on the GUI 700. The overlaying is enabled based on a video of the user 102 captured by cameras and further processed by the AI model in real-time. This has already been explained before in FIG. 1 and FIG. 2. As may be appreciated, the cameras capturing the user 102's pose and motion mid-way or along a long side of the smart mirror 100 may be adjusted for allowing a better aspect ratio of the user 102's pose.

Once the user 102 takes an initial position and pose to start performing the side push-ups, an AI model may determine whether the detected pose and position matches an initial pose and position mapped to the side push-ups activity. If the detected pose does not match with the initial pose and position, the AI model may instruct the user 102 to correct the initial pose and position. By way of an example, the AI model may instruct the user 102 by way of the message "pose incorrect."

Only when the initial pose and position taken by the user 102 is correct, a feedback, for example, "pose recognized," may be rendered to the user 102. Thereafter, the user 102 may be presented with the plurality of guidance steps by the virtual assistant 702. The user 102 may then need to follow the plurality of guidance steps as instructed in order to perform the side push-ups activity. Additionally, while the user 102 is performing the side push-ups activity, user performance parameters are also displayed along with on the GUI 700. As depicted in the GUI 700, a section 704 displays the total number of reps selected by the user 102 and the current number of reps performed, a section 706 displays a specific percentage of reps completed by the user 102, a section 708 displays a specific percentage of the activity completed by the user 102, a section 710 displays a heart rate of the user 102, and a section 712 displays the calories burnt by the user while performing the activity.

It may be noted that, display of the plurality of guidance steps and arrangement related to placement of visual information as discussed above, may be adjusted based on eye motion, voice-based input, a hand gesture, or position of the user so that the guidance steps and related information may be placed appropriately relative to the user 102's viewing angle and current position.

Figure 8:
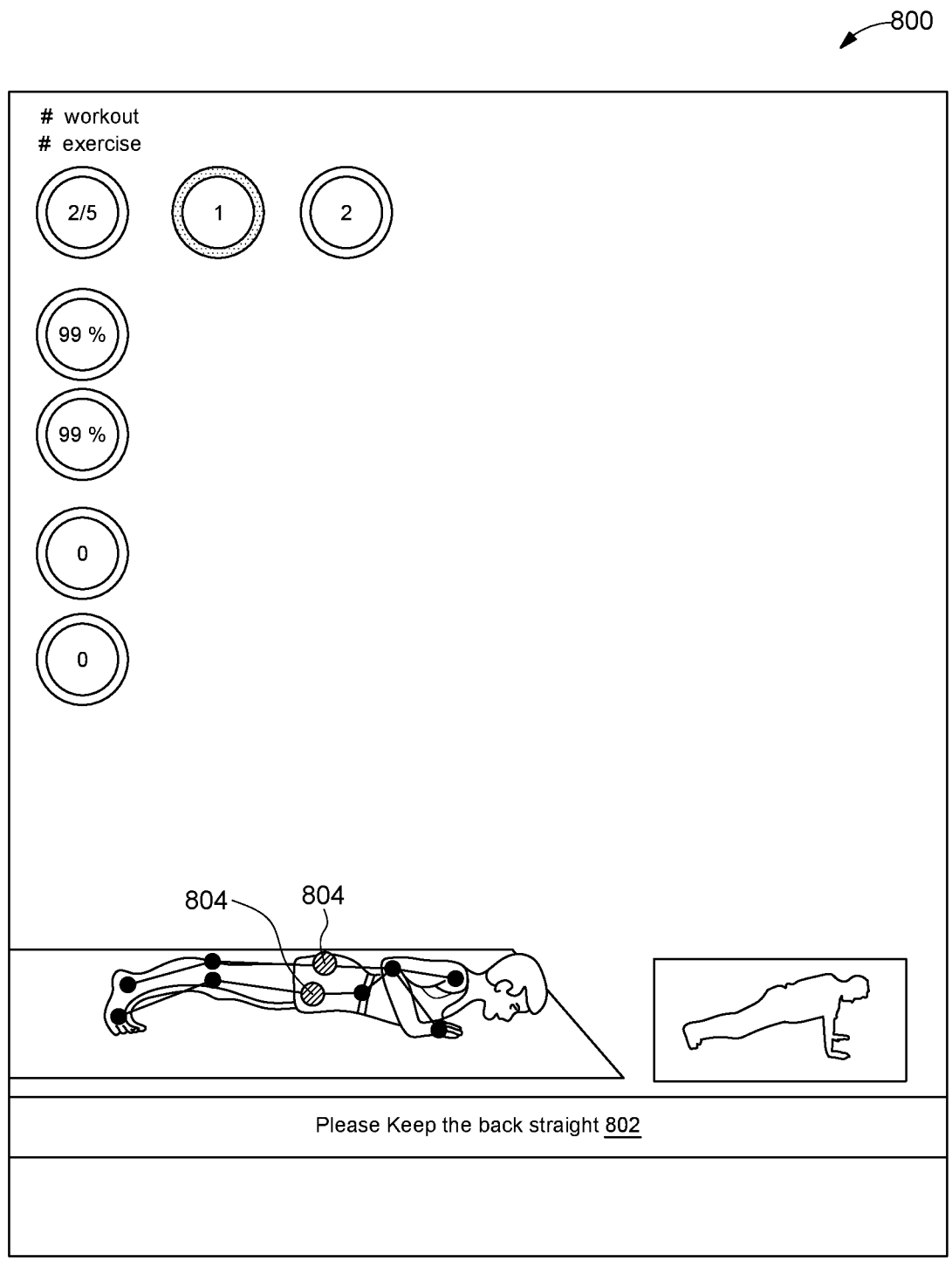
FIG. 8 illustrates a GUI depicting a feedback rendered to a user during performance of an activity by the user, in accordance with some exemplary embodiments.

Referring now to FIG. 8, a GUI 800 depicting a feedback rendered to a user during performance of an activity by the user 102 is illustrated, in accordance with some exemplary embodiments. With reference to FIG. 7, once the user 102 starts performing the side push-ups activity, the AI mode, in real-time, may process the live video capturing activity performance of the user 102. Thereafter, the AI model may, in real-time, determine user performance parameters and compare these with the target performance parameters to determine any deviations thereof. In the current exemplary embodiment, a deviation may correspond to the current pose of the user 102 while performing side push-ups being incorrect. More specifically, back of the user 102 may not be straight as required for side push-ups.

Thus, in response to the above detection of deviation, the AI model may provide feedback to the user 102 to correct his posture via the GUI 800. More specifically, the feedback may be displayed to the user 102 via the GUI 800 as a textual message 802. Additionally, specific skeletal points 804 overlayed over the user 102's reflection/video may be distinctly highlighted, for example, by changing the color of these skeletal points 804 or rendering specific graphical elements over these skeletal points 804. In addition to displaying the feedback on the GUI 800, audio message may also be rendered to the user 102, where the instruction "please keep the back straight" may be given to the user 102 in the aural form.

Figure 9A:
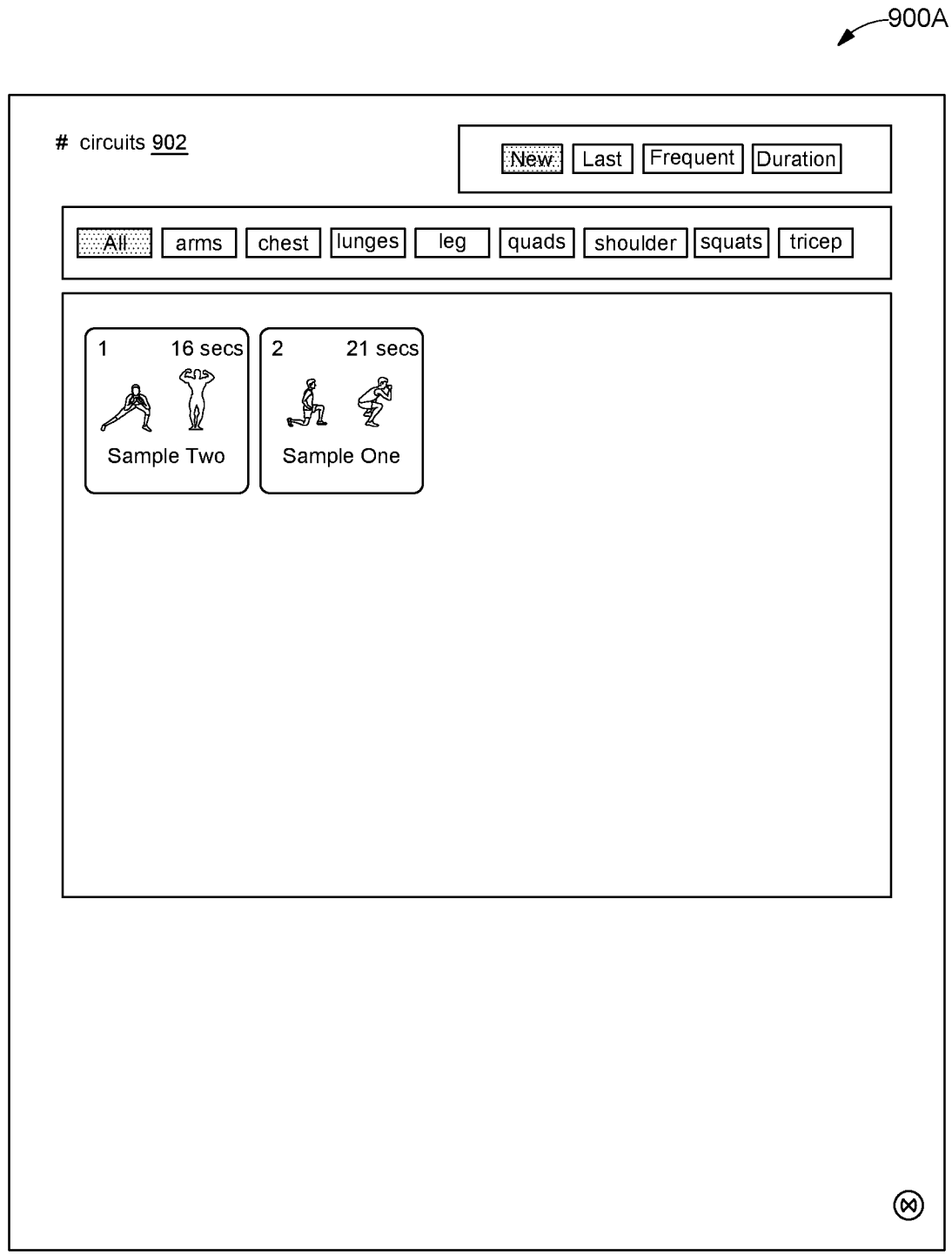
Figure 9B:
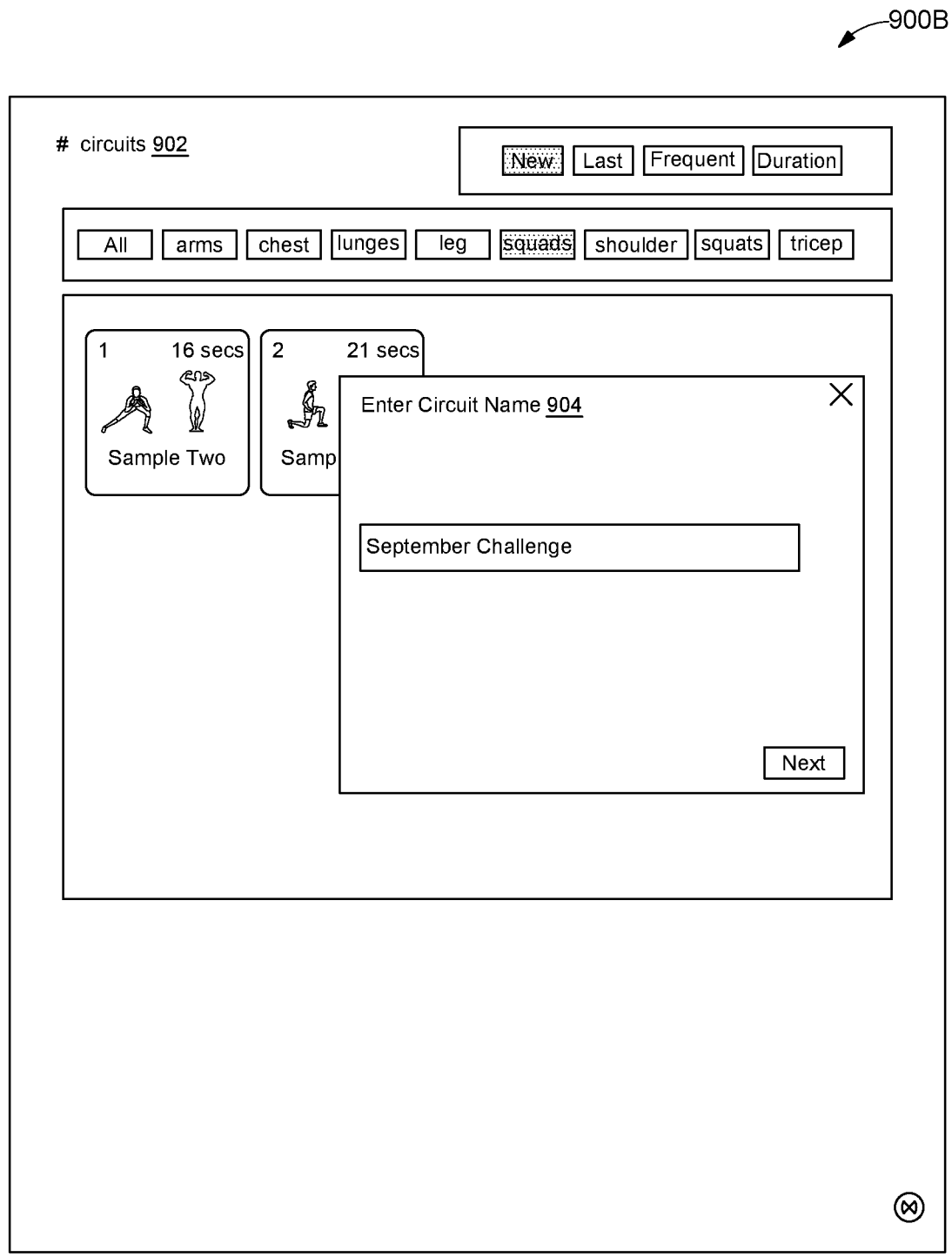

FIGS. 9A-9D illustrates GUIs 900A, 900B, 900C, and 900D depicting creation of a new activity training circuit and subsequent saving of the activity training circuit as a playlist, in accordance with some exemplary embodiments. With reference to FIG. 9A, the user 102 may select an option to create a new training circuit within a circuits section 902. When the user 102 selects an option to create a new circuit, a message box may be presented to the user asking the user 102 to provide a name for the new circuit. The user 102, for example, may assign a name "September Challenge" for the new circuit. The user 102 may also be able to select a set of activities that may be included in the new circuit. The set of activities that are selected in the current exemplary embodiment may include 'quick feet abduction,' 'cross behind lunge,' 'front uppercut,' 'squat thrusters, and 'drop squat.'

Figure 9C:
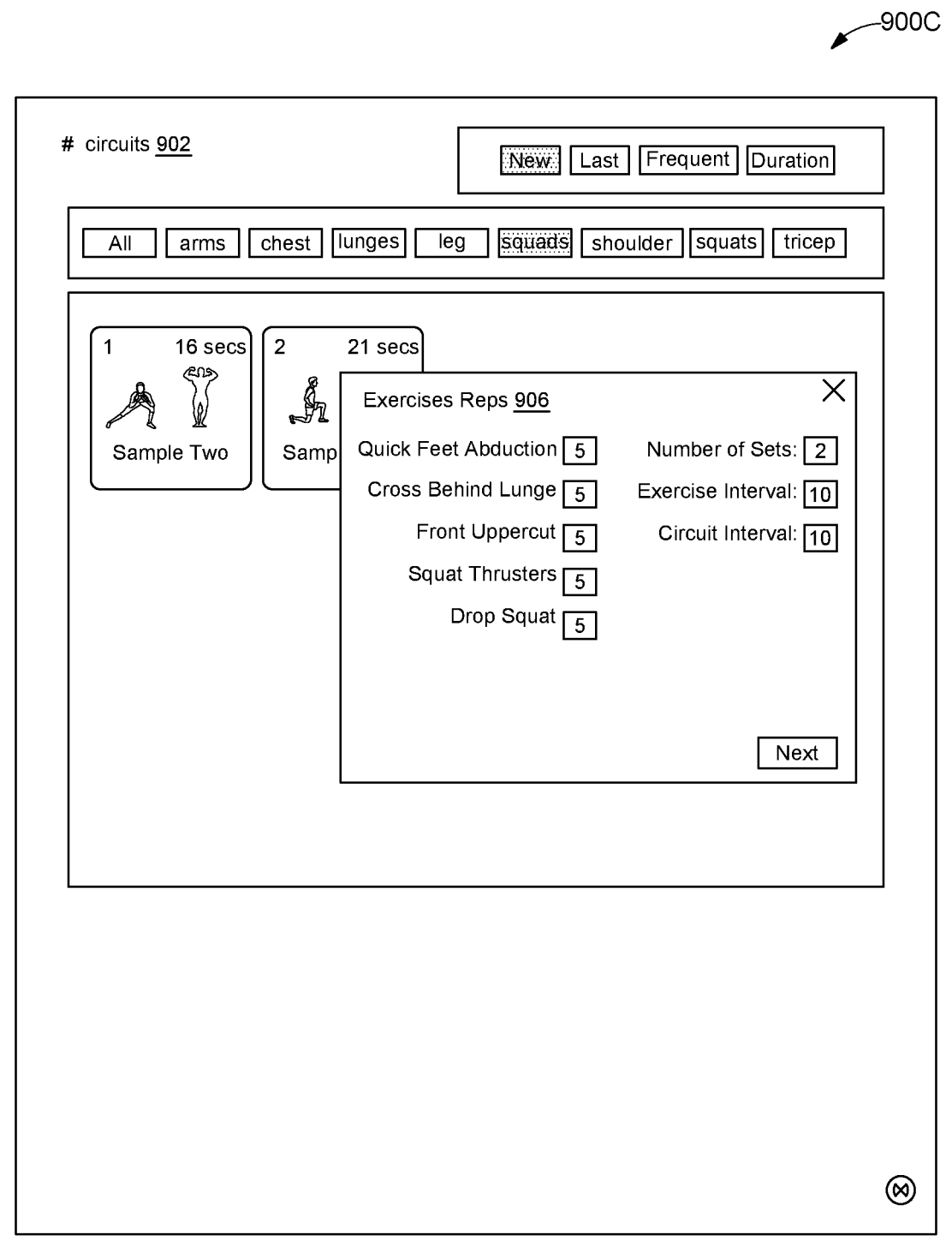
Figure 9D:
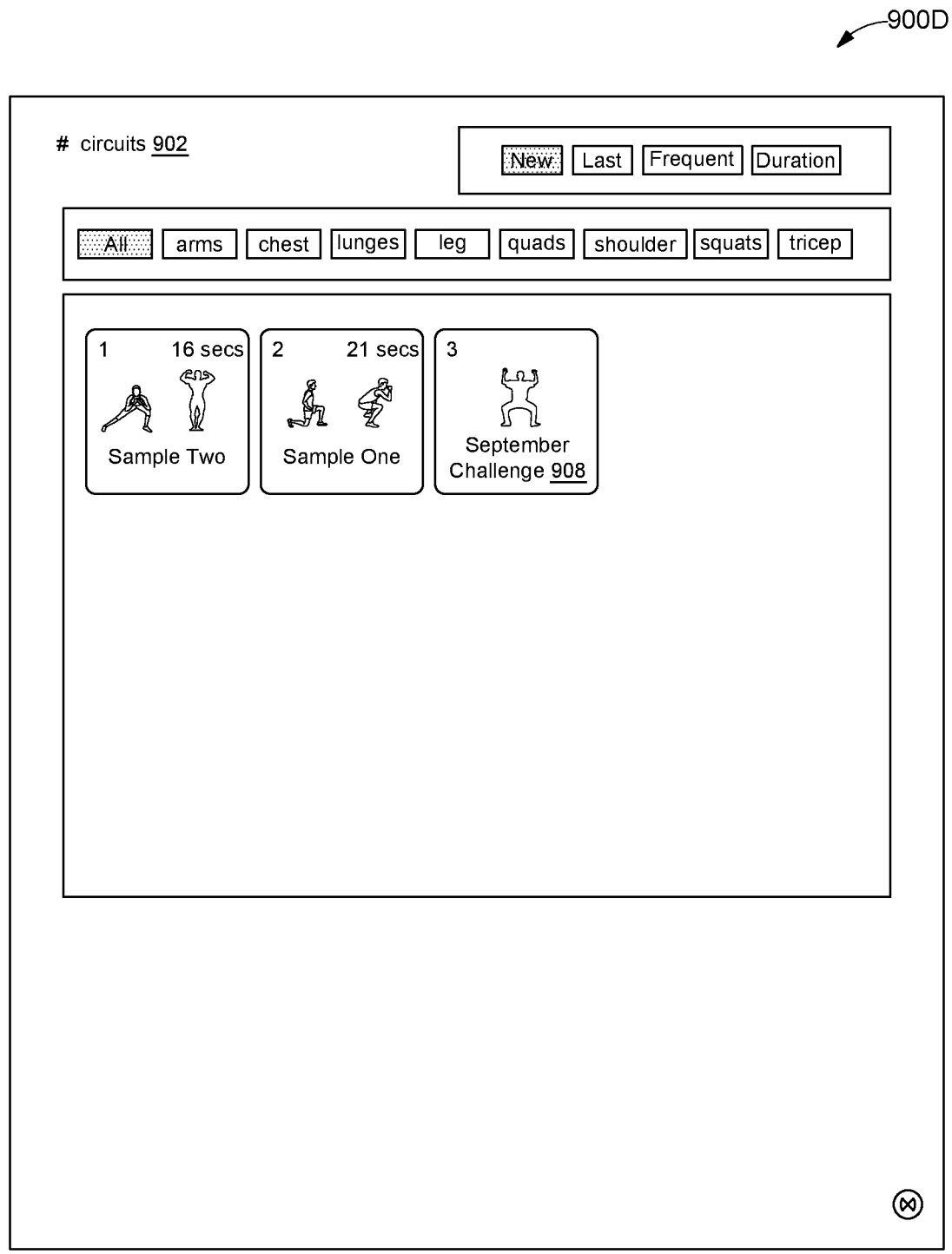

As shown in FIG. 9C, the user 102 may further add a set of attributes for each of the set of activities that have been selected to be included the new circuit. The attributes may be defined, for example, in an exercises reps section 906 that may include an option to select the number of counts for each of the set of activities. As depicted in the exercise reps section 906, the count for each of the set of activities mentioned above may be selected as 5. Further, the exercise reps section 906 the number of sets may be set as 2, exercise interval as 10 seconds, and the circuit interval as 10 seconds. On completion of selection of the set of attributes via the exercises rep section 906, the user 102 may save the new circuit. The new circuit may be added to an existing set of circuits as September challenge 908, as depicted in FIG. 9D.

Figure 10:
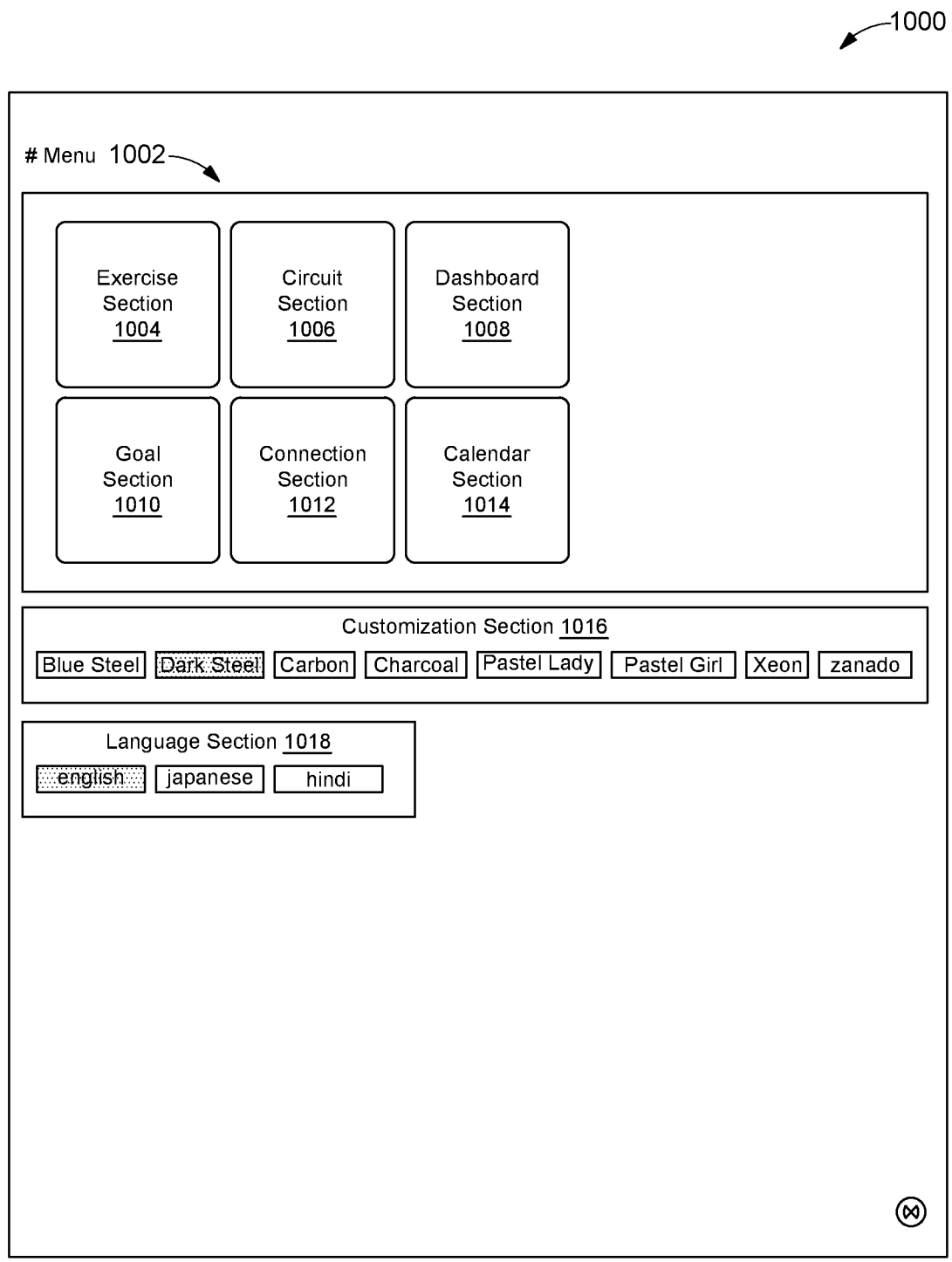
FIG. 10 illustrates a GUI depicting options associated with menu, customizations, and languages that may be provided to a user, in accordance with some exemplary embodiments.

Referring now to FIG. 10, a GUI 1000 depicting options associated with menu, customizations, and languages that may be provided to the user 102 is illustrated, in accordance with some exemplary embodiments. The GUI 1000 corresponds to a menu 1002 (or a home menu) that includes various shortcuts to exercise section 1004, circuit section 1006, dashboard section 1008, goals section 1010, connection section 1012, and a calendar section 1014 may be presented to the user 102. The user 102 may select an activity category and subsequently an activity to be performed using the exercise section 1004, the circuit section 1006 to create a new circuit or select an existing circuit, and the dashboard section 1008 to view various activities being performed by one or more users and their corresponding progress related to an activity over a period of time. The dashboard section 1008 may also display statistics related to activities being performed by the user 102 over a period of time. The statistics may relate to, for example, displaying reps performed by the user 102 managed as per date, time, volume, percentage accuracy, and review heart rate, calorie count.

Further, the goals section 1010 may enable the user 102 to set a personalized goal related to one or more activities for the user 102. The goal, for example, may be a new goal or a pending goal that needs to be achieved. The goal may also be set for a group of users. The connection section 1012 may enable the user 102 to connect to fitness gadgets and devices to enhance and share activity status of the user 102 with one or more users and third party smart devices. The user 102 may also be able to select a preferred list of communication interfaces to be used, for example, WiFi, Bluetooth, NFC, RFID, or infrared. Further, the calendar section 1014 may be used by the user 102 to schedule an activity for a particular day (or a schedule including multiple days) and remind the user 102 about his upcoming or pending activities.

The menu 1002 may further include a customization section 1016, using which, the user 102 may select one or more display themes for customizing the look and feel of various GUIs of the smart mirror 100 and/or the display 200. The themes, for example, may be set to one of blue steel, dark steel, carbon, charcoal or the like. The menu 1002 may also provide the user 102 with an option to select a source language from a language section 1018. The user 102 may the use the source language for communicating for providing voice based instructions to the smart mirror 100. Additionally, the source language may also be used as the language used to display various content on the smart mirror 100 and/or the display 200.

Figure 11:
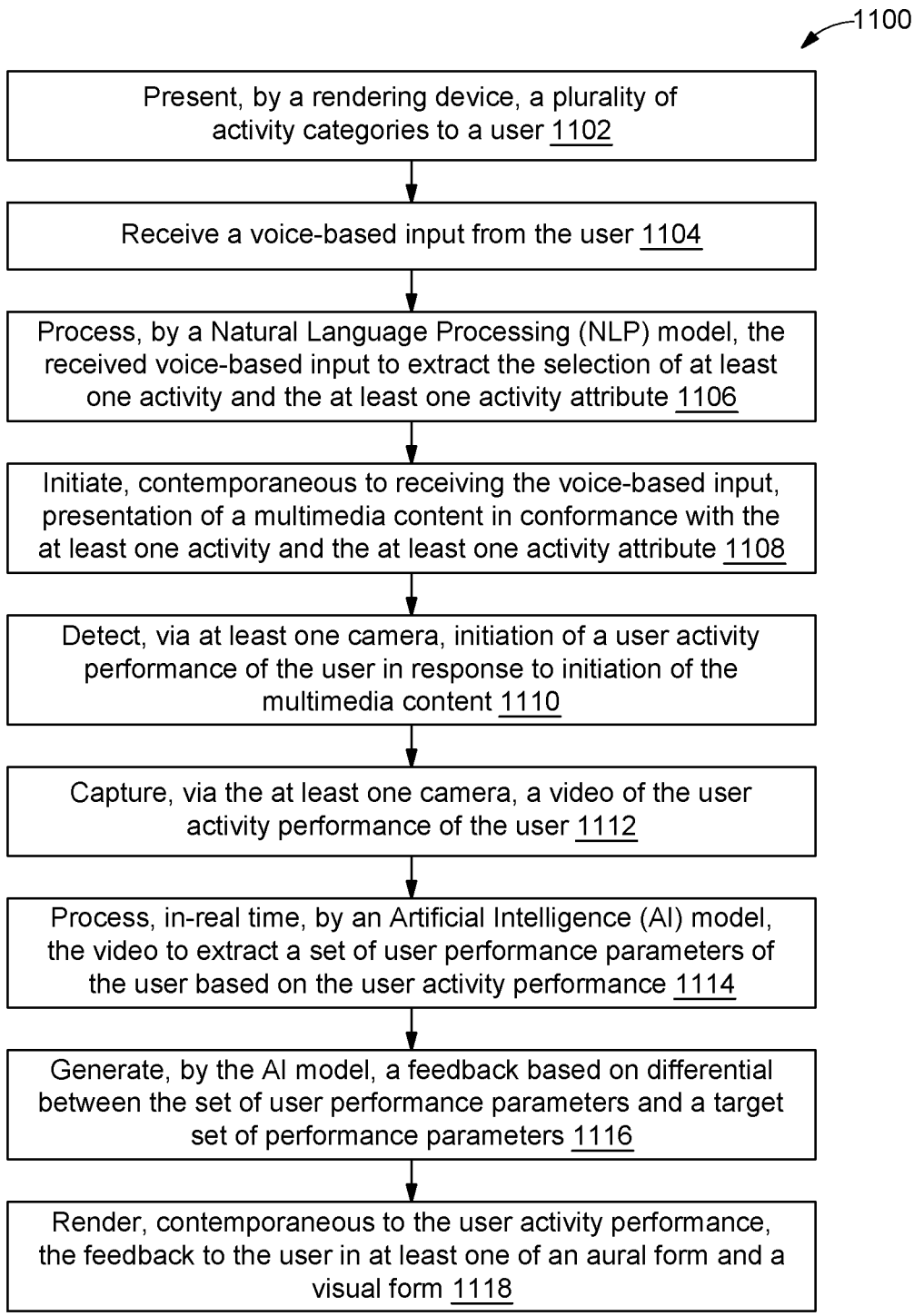
FIG. 11 illustrates a flowchart of a method for providing an AI assisted activity training, in accordance with some embodiments.

Referring now to FIG. 11, a flowchart of a method 1100 for providing an AI assisted activity training is illustrated, in accordance with some embodiments. The method 1100 includes presenting, by a rendering device, a plurality of activity categories to a user, at step 1102. Each of the plurality of activity categories may include a plurality of activities, and the plurality of activity categories may be presented as multimedia content. The rendering device may be a fitness mirror, a smart fitness mirror, a display screen, a mobile device, such as, but not limited to a mobile phone, a tablet, a smartwatch, a laptop, or the like. Further, the user may be personal coach, trainer, gym activity expert, physical therapist, occupational therapist, physical education teacher, martial arts teacher, choreographer, sports personality, team coach, demonstrators, and other trainers in health and fitness.

Further, based on the presented plurality of activity categories, the method 1100 may receive a voice-based input from the user, at step 1104. The voice-based input may include an activity training plan that includes a selection of at least one activity from at least one of the plurality of activity categories. Further, at least one activity attribute may associate with each of the at least one activity may also be received at step 1104. By way of an example, the activity attributes may include one or more of, but are not limited to number of reps, number of reps, and an interval in which the activity is to be performed. Also, a level of expertise for the user for performing the exercise may be selected under the at least one activity attribute. The level of expertise may be a beginner level or an advanced level. The voice-based input may be received in a source language of the user. The source language may include, but is not limited to English, Japanese, or Hindi.

Upon receiving the voice-based input, an NLP model may process the received voice-based input to extract the selection of at least one activity and the at least one activity attribute at step 1106. For example, the voice-based input "select Front Hook" may be processed by the NLP model to select and present a Front Hook exercise. Following the selection of the Front Hook exercise, attributes such as "Number of Reps", "Number of Sets" and "Interval" may be provided. Also, a determination of whether the user is a beginner or at an advanced level may be selected.

Contemporaneous to receiving the voice-based input, presentation of multimedia content in conformance with the at least one activity and the at least one activity attribute may be initiated at step 1108. Upon presentation of the multimedia content, at step 1110, an initiation of a user activity performance of the user may be detected via the at least one camera. While the user is performing the activity, a video of the user activity performance of the user may be captured via the at least one camera, at step 1112. Thereafter, the video may be processed in real-time by an AI model to extract a set of user performance parameters of the user based on the user activity performance at step 1114. Further, the AI model may be used to generate a feedback based on differential between the set of user performance parameters and a target set of performance parameters, at step 1116. Contemporaneous to the user activity performance, the feedback may be rendered to the user in at least one of an aural form, a visual form, or as haptic feedback at step 1118. This has already been explained in detail in conjunction with FIGS. 1-4.

Figure 12:
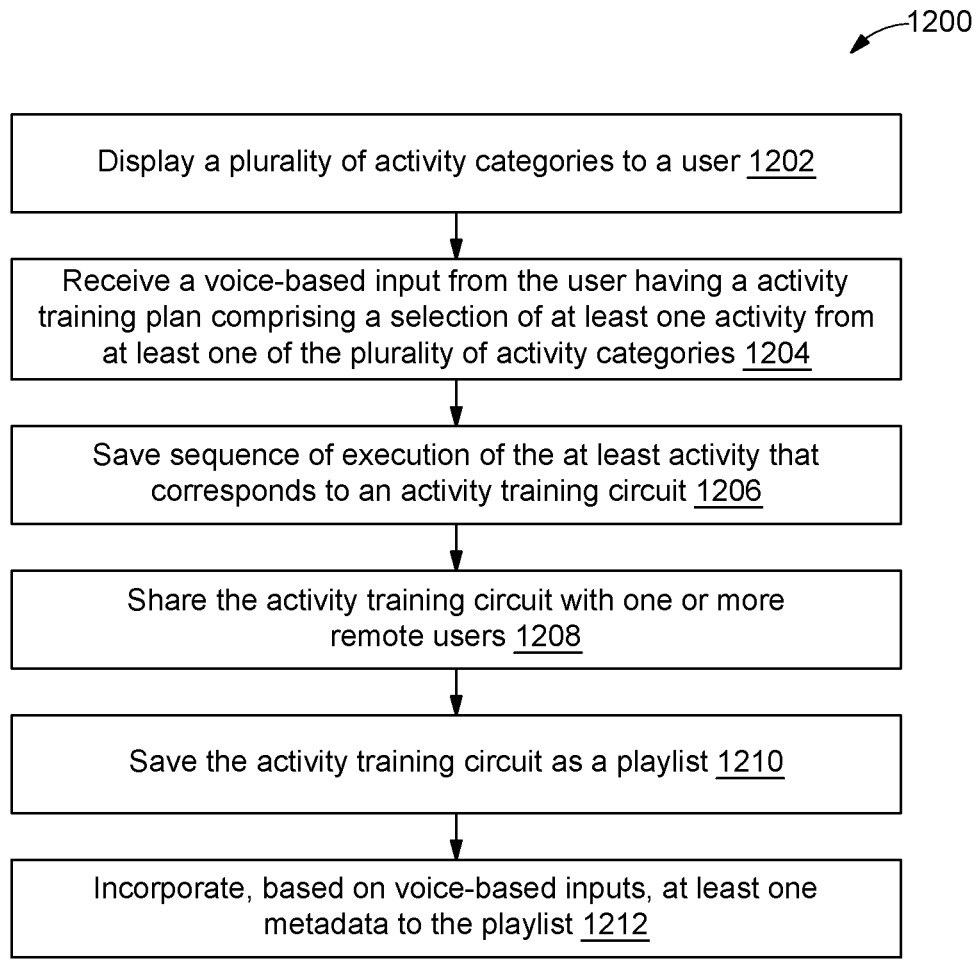
FIG. 12 illustrates a flowchart of a method for creating an activity training circuit, in accordance with some embodiments.

Referring now to FIG. 12, a flowchart of a method 1200 for creating an activity training circuit is illustrated, in accordance with some embodiments. The method 1200 may display a plurality of activity categories to the user at step 1202. The user may choose to perform an activity using a voice-based input. The voice-based input may be received from the user at step 1204. The voice-based input may include an activity training plan that includes selection multiple activities and a selection of sequence of execution of the one or more activities. The activity training plan may correspond to an activity training circuit. Thereafter, the activity training circuit may be shared with one or more remote users at step 1208. Further, the activity training circuit may be saved as a playlist at step 1210. At step 1212, based on the voice-based inputs, at least one metadata may be incorporated to the playlist. The metadata may include one or more of, but is not limited to an intensity, count, enjoyment factor, projected calorie burn, target muscle group, target body part, age group, weight, gender, time taken, or expected heart rate. This has already been explained in detail in conjunction with FIGS. 1-4.

Figure 13:
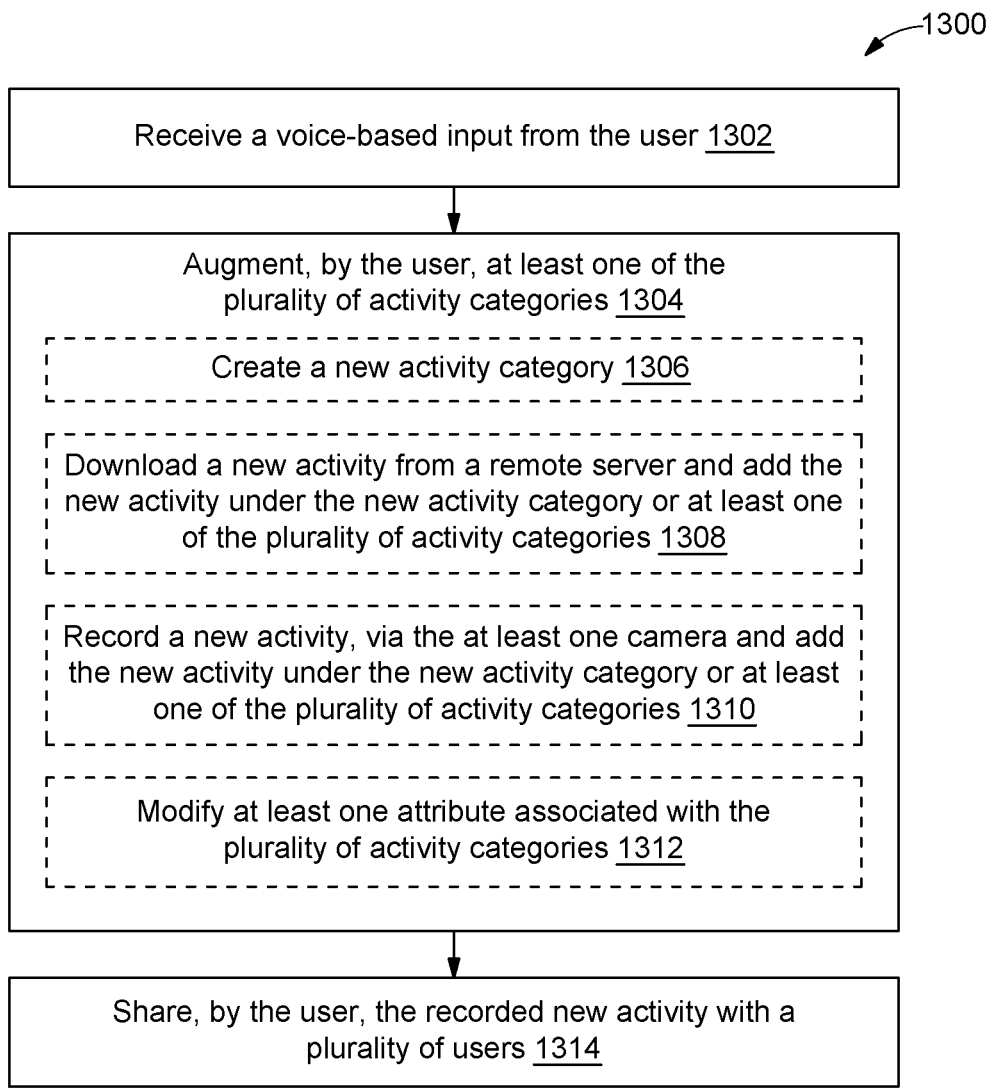
FIG. 13 illustrates a flowchart of a method for augmenting activity categories, in accordance with some embodiments.

Referring now to FIG. 13, a flowchart of a method 1300 for augmenting activity categories is illustrated, in accordance with some embodiments. A voice-based input may be received from the user at step 1302. Based on the voice-based input, the user may augment at least one of the plurality of activity categories, at step 1304. Augmenting the at least one of the plurality of activity categories may include steps 1306 to 1312, which may be executed in sequence, in parallel, or completely independent of each other.

At step 1306, a new activity category may be created. The new activity may be downloaded from a remote server and the new activity may be added under the new activity category or at least one of the plurality of activity categories at step 1308. Alternatively, a new activity may be recorded via the at least one camera and may subsequently be added under the new activity category or at least one of the plurality of activity categories at step 1310. For example, the one or more cameras configured with the smart mirror 100 may be used as a recording tool for creating new fitness content and associated instructions for the activity to be performed. In some configurations, at least one attribute associated with the plurality of activity categories may be modified, at step 1312. The recorded new activity may be shared by the user at step 1314 with other users or on social media platforms.

In some scenarios, the user who augments one or more of the activity categories based on his new acquired skill in performing a new activity may be a trainer. Upon augmenting the activity category with the new category, trainer may share the recorded new activity with one or more users or some social media platform for a predetermined fees.

Figure 14:
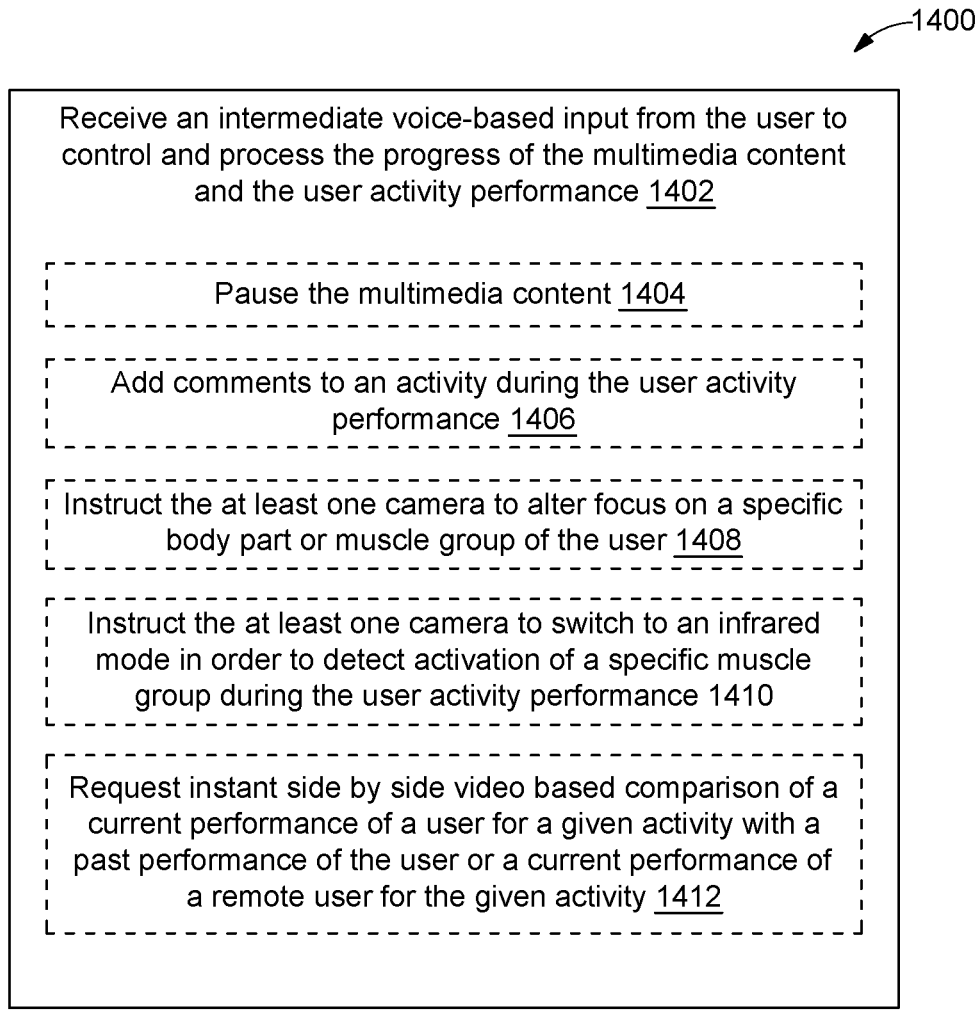
FIG. 14 illustrates a flowchart of a method for controlling and processing progress of multimedia content and user activity performance based on received intermediate voice-based input, in accordance with some embodiments.

Referring now to FIG. 14, a flowchart of a method 1400 for controlling and processing progress of multimedia content and user activity performance based on received intermediate voice-based input is illustrated, in accordance with some embodiments. The method 1400 may receive an intermediate voice-based input from the user to control and process the progress of the multimedia content and the user activity performance at step 1402.

Controlling and processing of the multimedia content may include, for example, pausing the multimedia content, at step 1404, adding comments to an activity during the user activity performance, at step 1406. For example, when the user is performing the activity and feels that the performed activity is strenuous and that the user is unable to cope, the user may issue the intermediate voice-based input to pause the display of the multimedia content and may further add comments to the activity being strenuous. Further, at least one camera may be instructed to alter focus on a specific body part or muscle group of the user, at step 1408. For example, the user may generate the voice-based input to instruct the at least one camera to alter focus on a specific muscle group of the user in order to determine the degree of muscle activation.

Also, the at least one camera may be instructed to switch to an infrared mode in order to detect activation of a specific muscle group during the user activity performance, at step 1410. Further, at step 1412, a request for an instant side by side video based comparison of a current performance of a user for a given activity with a past performance of the user or a current performance of a remote user for the given activity may be raised. The side-by-side video may enable and help the user to compare and determine his progress for performing the activity and also determine how the user fares at the performing the activity amongst plurality of users.

Figure 15:
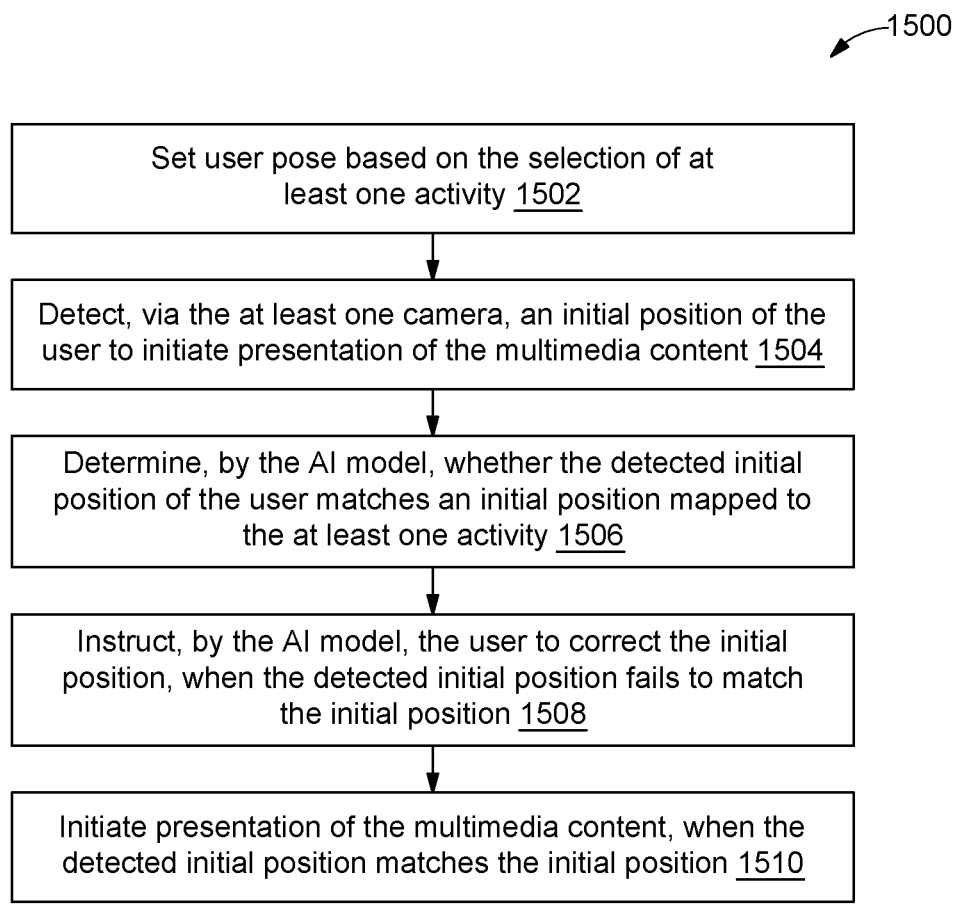
FIG. 15 illustrates a flowchart of a method for determining an initial pose of the user and instructing user to adjust initial position of the user for presentation of multimedia content, in accordance with some embodiments.

Referring now to FIG. 15, a flowchart of a method 1500 for determining an initial pose of the user and instructing user to adjust initial position of the user for presentation of multimedia content is illustrated, in accordance with some embodiments. In the method 1500, at step 1502, the user may set a user pose based on the selection of at least one activity. An initial position of the user may be detected to initiate presentation of the multimedia content, at step 1504. Further, an AI model may be used to determine whether the detected initial position of the user matches an initial position mapped to the at least one activity or not, at step 1506. When the detected initial position fails to match the initial position, the AI model may instruct the user to correct the initial position, at step 1508. However, when the detected initial position matches the initial position, presentation of the multimedia content may be initiated at step 1510. This has already been explained in detail in conjunction with FIGS. 1, 2, and 7.

Figure 16:
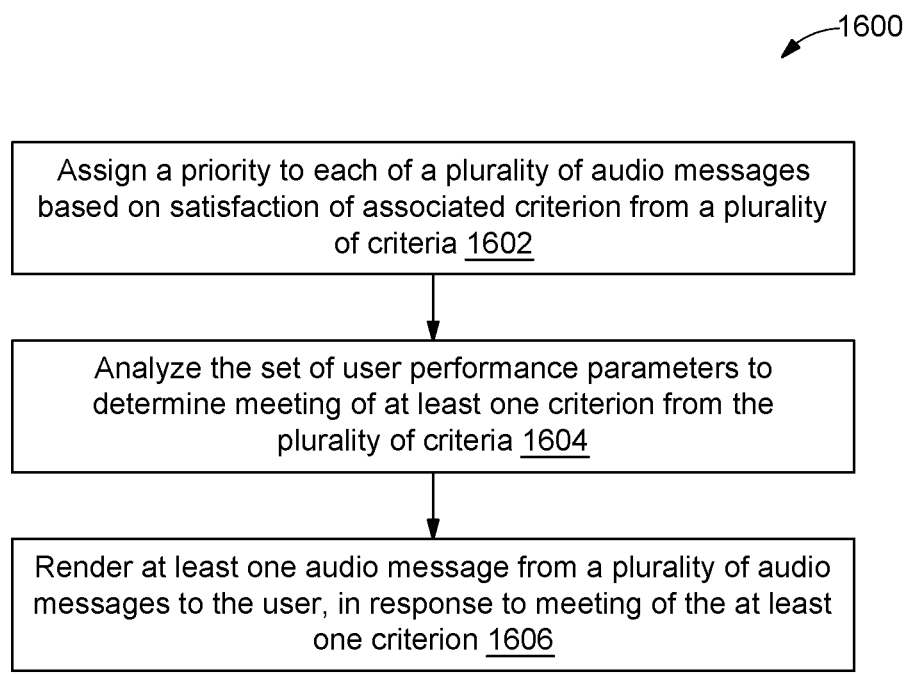
FIG. 16 illustrates a flowchart of a method for prioritizing and subsequently rendering feedback to a user based on a plurality of criteria, in accordance with some embodiments.

Referring now to FIG. 16, a flowchart of a method 1600 for prioritizing and subsequently rendering feedback to a user based on a plurality of criteria is illustrated, in accordance with some embodiments. The method 1600 includes assigning a priority to each of a plurality of audio messages based on satisfaction of associated criterion from a plurality of criteria at step 1602. The plurality of audio messages may either be predefined and thus prestored in a memory of the smart mirror 100 (for example, the memory 418). Alternatively or additionally, one or more audio messaged may be generated on the fly by an AI model (for example, the AI model 122). The method 1600 further includes analyzing the set of user performance parameters to determine meeting of at least one criterion from the plurality of criteria at step 1604. The method 1600 includes rendering at least one audio message from a plurality of audio messages to the user, in response to meeting of the at least one criterion. The at least one audio message corresponds to the at least one criterion. The at least one audio message may be rendered in the source language. It may be noted that when the AI model generated messages on the fly, the AI model may itself evaluate the current conditions to intelligently determine the audio message to be rendered according to the evaluated priority or situation.

To elaborate further, timing and duration of an utterance related to the feedback for the user may be crucial, as may be appreciated. For example, when the user is performing the activity fast, some feedback messages may get obsolete before being generated and spoken. Additionally, certain feedback messages may become repetitive and unnatural. Further, some of the feedback messages may have a higher priority, for example, feedback messages related to warnings and errors. The priority of the messages may be handled based on priority queues. Also, the AI mode may be used to give a more natural dialogue to the feedback messages.

Figure 17:
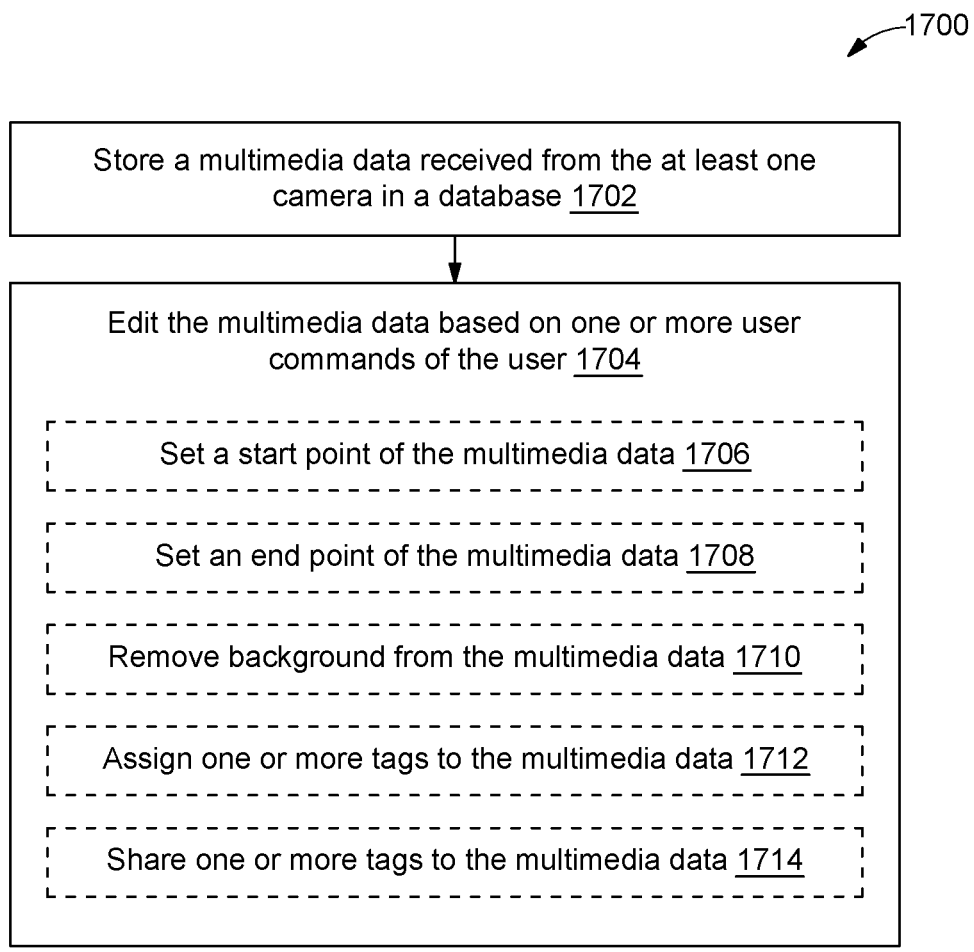
FIG. 17 illustrates a flowchart of a method for editing a multimedia data capturing user activity performance, in accordance with some embodiments.

With reference to FIG. 17, a flowchart of a method 1700 for editing a multimedia data capturing user activity performance is illustrated, in accordance with some embodiments. The method 1700 may store the multimedia data received from the at least one camera in a database, at step 1702. The multimedia data may be edited based on one or more commands of the user, at step 1702. The step 1702 may further include steps 1706 to 1714, which may be executed in sequence, in parallel, or completely independent of each other. The user command may be at least one of a text command, voice command, touch command, or a visual gesture.

The one or more user commands may include at least one of setting a start point of the multimedia data, at step 1704, setting an end point of the multimedia data, at step 1706. Further, background may be removed from the multimedia data, at step 1708. One or more tags may be assigned to the multimedia data at step 1712 and the multimedia data may be shared with a set of other users at step 1710.

As may be appreciated, in some configurations, the user and/or real trainer using the smart mirror 100 may use the voice-based input to crop or highlight the activity and/or guidelines provided by the virtual assistant, add voice or text feedback on the smart mirror 400. Additionally, the user 102 and the instructor may be permitted to add or remove background image as used in the smart mirror. The voice-based input may be used to create and save playlists, add metadata to the playlists, add comments using speech-to-text mechanism and audio feedback to the playlists and the activities, record a new activity category, edit and clip the activity to be performed, tag an exercise with hashtags, for example, type of exercise, muscle groups or level of difficulty, replace an exercise clip with an alternative version, share playlists and exercises with other users, dictate a message for another user when sharing the playlists.

As will be also appreciated, the above-described techniques may take the form of computer or controller implemented processes and apparatuses for practicing those processes. The disclosure can also be embodied in the form of computer program code containing instructions embodied in tangible media, such as floppy diskettes, solid state drives, CD-ROMs, hard drives, or any other computer-readable storage medium, wherein, when the computer program code is loaded into and executed by a computer or controller, the computer becomes an apparatus for practicing the invention. The disclosure may also be embodied in the form of computer program code or signal, for example, whether stored in a storage medium, loaded into and/or executed by a computer or controller, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

Thus, the disclosed method and system try to overcome the problem of using specific gestures or issuing instructions using input based devices for setting instructions and graphics to be displayed while performing an activity using a smart mirror. The method and system may present activity categories to the user and the user may chose the activity to be performed using a voice-based input in a source language. Further, an NLP model may process the voice-based input to extract an activity selected by the user. Further, the disclosed system and method initiates presentation of multimedia content in conformance with the activity. A video of the user activity may be captured using a camera and the video is processing using the AI model to extract user performance parameters. The AI model may generate a feedback based on the user performance parameters and may render the feedback on the smart mirror.

As will be appreciated by those skilled in the art, the techniques described in the various embodiments discussed above are not routine, or conventional, or well understood in the art. The techniques discussed above may provide presenting, by a rendering device, a plurality of activity categories to a user. Each of the plurality of activity categories may include a plurality of activities. The plurality of activity categories may be presented as multimedia content. The technique may receive a voice-based input from the user. The voice-based input may include an activity training plan comprising a selection of at least one activity from at least one of the plurality of activity categories and at least one activity attribute associated with each of the at least one activity, and wherein the voice-based input is in a source language. Further, the technique may process, by a Natural Language Processing (NLP) model, the received voice-based input to extract the selection of at least one activity and the at least one activity attribute. The NLP model may be configured using a single language, and wherein the single language is an intermediate language. Contemporaneous to receiving the voice-based input, the technique may initiate presentation of a multimedia content in conformance with the at least one activity and the at least one activity attribute. The multimedia content may include a plurality of guidance steps performed by a virtual assistant corresponding to the at least one activity. Further, the technique may detect, via at least one camera, initiation of a user activity performance of the user in response to initiation of the multimedia content. The user activity performance of the user at a given time may include imitation of one of the at least one activity. Further, the technique may capture, via the at least one camera, a video of the user activity performance of the user. The at least one camera is placed at distributed locations. The technique may process in-real time, by an Artificial Intelligence (AI) model, the video to extract a set of user performance parameters of the user based on the user activity performance. The technique may use the AI model to generate a feedback based on differential between the set of user performance parameters and a target set of performance parameters. Contemporaneous to the user activity performance, the technique may render the feedback to the user in at least one of an aural form, a visual form, or as a haptic feedback.

As will be appreciated by those skilled in the art, the techniques described in the various embodiments discussed above are not routine, or conventional, or well understood in the art. The techniques discussed above may provide receiving, via a communication device, a user input from a user in a source language. The user input may be least one of a textual input and a verbal input. The technique may translate the user input, using a machine translation model, to generate a plurality of translated user inputs in an intermediate language. A confidence score may be associated with each of the plurality of translated user inputs. Each of the plurality of translated user inputs may be in text form. The technique may generate for the plurality of translated user inputs a plurality of sets of intermediate input vectors in the intermediate language using the SNLP model configured only using the intermediate language. The technique may process the plurality of sets of intermediate input vectors in the intermediate language using at least one of a plurality of predefined mechanisms to identify a predetermined response. The technique may translate the predetermined response to generate a translated response. The translated response may be rendered to the user.

In light of the above-mentioned advantages and the technical advancements provided by the disclosed method and system, the claimed steps as discussed above are not routine, conventional, or well understood in the art, as the claimed steps enable the following solutions to the existing problems in conventional technologies. Further, the claimed steps clearly bring an improvement in the functioning of the device itself as the claimed steps provide a technical solution to a technical problem.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A method for Artificial Intelligence (AI) assisted activity training, the method comprising:
   presenting, by a rendering device, a plurality of activity categories to a user, wherein each of the plurality of activity categories comprises a plurality of activities, and wherein the plurality of activity categories are presented as multimedia content;
   receiving a voice-based input from the user, wherein the voice-based input comprises an activity training plan comprising a selection of at least one activity from at least one of the plurality of activity categories and at least one activity attribute associated with each of the at least one activity, and wherein the voice-based input is in a source language;
   processing, by a Natural Language Processing (NLP) model, the received voice-based input to extract the selection of at least one activity and the at least one activity attribute, wherein the NLP model is configured using a single language, and wherein the single language is an intermediate language;
   initiating, contemporaneous to receiving the voice-based input, presentation of a multimedia content in conformance with the at least one activity and the at least one activity attribute, wherein the multimedia content comprises a plurality of guidance steps performed by a virtual assistant corresponding to the at least one activity;
   detecting, via at least one camera, initiation of a user activity performance of the user in response to initiation of the multimedia content, wherein the user activity performance of the user at a given time comprises imitation of one of the at least one activity;
   capturing, via the at least one camera, a video of the user activity performance of the user, wherein the at least one camera is placed at distributed locations;
   processing, in-real time, by an Artificial Intelligence (AI) model, the video to extract a set of user performance parameters of the user based on the user activity performance, wherein the set of user performance parameters comprises speed of a current activity performance, number of repetitions completed, overall completion of an activity circuit, third-party smart device information, pulse rate of the user, blood pressure of the user, and motion of the user;

generating, by the AI model, a feedback based on differential between the set of user performance parameters and a target set of performance parameters, wherein the target set of performance parameters comprises speed of the target activity performance, blood pressure, target number of repetitions, target pulse rate of the user, and target motion of the user; and rendering, contemporaneous to the user activity performance, the feedback to the user in at least one of an aural form, a visual form, or as a haptic feedback.

2. The method of claim 1, wherein the at least one activity attribute comprises at least one of sequence of execution of the at least activity, a number of sets for performing each of the at least one activity, a count for each of the at least one activity in each of the sets, duration of performing each of the at least one activity, rest period between each of the sets, intensity of performing each of the at least one activity, difficulty level of performing each of the at least one activity, or pace of performing each of the at least one activity.

3. The method of claim 2, wherein the sequence of execution of the at least one activity corresponds to an activity training circuit.

4. The method of claim 3, further comprising sharing the activity training circuit with one or more remote users.

5. The method of claim 3, further comprising:
saving the activity training circuit as a playlist; and
incorporating, based on voice-based inputs, at least one metadata to the playlist, wherein the metadata corresponds to an intensity, count, enjoyment factor, projected calorie burn, target muscle group, target body part, age group, weight, gender, time taken, or expected heart rate.

6. The method of claim 1, wherein the feedback comprises at least one of:
calories burnt, maximum count of the at least one activity performed, maximum time spent for the at least one activity during a previous activity session of the user, incorrect posture or pace of the user while performing the at least one activity, correct posture or pace to perform the at least one activity, absolute activity performance proficiency of the user, relative activity performance proficiency of the user, best time taken to perform the at least one activity, or warnings associated with biometric parameters of the user.

7. The method of claim 1, further comprising augmenting, by the user, at least one of the plurality of activity categories, wherein augmenting comprises at least one of:
creating a new activity category;
downloading a new activity from a remote server and adding the new activity under the new activity category or at least one of the plurality of activity categories;
recording a new activity, via the at least one camera and adding the new activity under the new activity category or at least one of the plurality of activity categories; and
modifying at least one attribute associated with the plurality of activity categories, wherein the at least one attribute comprises name, priority, number of activities with an activity category, or display position.

8. The method of claim 7, further comprising:
sharing, by the user, the recorded new activity with a plurality of users, wherein the recorded new activity is shared for a predetermined fees; and presenting on a leader board the at least one attribute associated with each of the plurality of activity categories for each of the plurality of users for training and feedback.

9. The method of claim 1, further comprising:
receiving an intermediate voice-based input from the user to control and process progress of the multimedia content and the user activity performance, wherein the intermediate voice-based input comprises at least one of:
pausing the multimedia content;
adding comments to an activity during the user activity performance;
instructing the at least one camera to alter focus on a specific body part or muscle group of the user;
instructing the at least one camera to switch to an infrared mode in order to detect activation of a specific muscle group during the user activity performance;
instructing the at least one camera to switch to an infrared mode in order to detect activation of a specific muscle group during the user activity performance; and
requesting instant side by side video based comparison of a current performance of a user for a given activity with a past performance of the user or a current performance of a remote user for the given activity.

10. The method of claim 1, wherein generating the feedback in the aural form comprises:
assigning a priority to each of a plurality of audio messages based on satisfaction of associated criterion from a plurality of criteria;
analyzing the set of user performance parameters to determine meeting of at least one criterion from the plurality of criteria; and
rendering at least one audio message from a plurality of audio messages to the user, in response to meeting of the at least one criterion, wherein the at least one audio message corresponds to the at least one criterion, and wherein the at least one audio message is rendered in the source language.

11. The method of claim 1, further comprising:
detecting, via the at least one camera, an initial position of the user to initiate presentation of the multimedia content;
determining, by the AI model, whether the detected initial position of the user matches an initial position mapped to the at least one activity;
instructing, by the AI model, the user to correct the initial position, when the detected initial position fails to match the initial position; and
initiating presentation of the multimedia content, when the detected initial position matches the initial position.

12. The method of claim 1, further comprising:
storing a multimedia data received from the at least one camera in a database; and
editing the multimedia data based on one or more user commands of the user, wherein the user command is at least one of a text command, voice command, touch command, or a visual gesture, wherein the one or more user commands comprise at least one of:
setting a start point of the multimedia data;
setting an end point of the multimedia data;
removing background from the multimedia data;
assigning one or more tags to the multimedia data; and
sharing the multimedia data with a set of other users.

13. A system for Artificial Intelligence (AI) assisted activity training, the system comprising:
a processor; and a memory communicatively coupled to the processor, wherein the memory stores processor-executable instructions, which, on execution, causes the processor to:

present, by a rendering device, a plurality of activity categories to a user, wherein each of the plurality of activity categories comprises a plurality of activities, and wherein the plurality of activity categories are presented as multimedia content;

receive a voice-based input from the user, wherein the voice-based input comprises an activity training plan comprising a selection of at least one activity from at least one of the plurality of activity categories and at least one activity attribute associated with each of the at least one activity, and wherein the voice-based input is in a source language;

process, by a Natural Language Processing (NLP) model, the received voice-based input to extract the selection of at least one activity and the at least one activity attribute, wherein the NLP model is configured using a single language, and wherein the single language is an intermediate language;

initiate, contemporaneous to receiving the voice-based input, presentation of a multimedia content in conformance with the at least one activity and the at least one activity attribute, wherein the multimedia content comprises a plurality of guidance steps performed by a virtual assistant corresponding to the at least one activity;

detect, via at least one camera, initiation of a user activity performance of the user in response to initiation of the multimedia content, wherein the user activity performance of the user at a given time comprises imitation of one of the at least one activity;

capture, via the at least one camera, a video of the user activity performance of the user, wherein the at least one camera is placed at distributed locations;

process, in-real time, by an Artificial Intelligence (AI) model, the video to extract a set of user performance parameters of the user based on the user activity performance, wherein the set of user performance parameters comprises speed of a current activity performance, number of repetitions completed, overall completion of an activity circuit, third-party smart device information, pulse rate of the user, blood pressure of the user, and motion of the user;

generate, by the AI model, a feedback based on differential between the set of user performance parameters and a target set of performance parameters, wherein the target set of performance parameters comprises speed of the target activity performance, blood pressure, target number of repetitions, target pulse rate of the user, and target motion of the user; and render, contemporaneous to the user activity performance, the feedback to the user in at least one of an aural form, a visual form, or as haptic feedback.

14. The system of claim 13, wherein the at least one activity attribute comprises at least one of sequence of execution of the at least activity, a number of sets for performing each of the at least one activity, a count for each of the at least one activity in each of the sets, duration of performing each of the at least one activity, rest period between each of the sets, intensity of performing each of the at least one activity, difficulty level of performing each of the at least one activity, or pace of performing each of the at least one activity.

15. The system of claim 14, wherein the sequence of execution of the at least activity corresponds to an activity training circuit.

16. The system of claim 15, wherein the processor-executable instructions further cause the processor to share the activity training circuit with one or more remote users.

17. The system of claim 13, wherein the feedback comprises at least one of:
calories burnt, maximum count of the at least one activity performed, maximum time spent for the at least one activity during a previous activity session of the user, incorrect posture or pace of the user while performing the at least one activity, correct posture or pace to perform the at least one activity, absolute activity performance proficiency of the user, relative activity performance proficiency of the user, best time taken to perform the at least one activity, or warnings associated with biometric parameters of the user.

18. The system of claim 13, wherein the processor-executable instructions further cause the processor to augment, in response to an action by the user, at least one of the plurality of activity categories, wherein augmenting comprises at least one of:
creating a new activity category;
downloading a new activity from a remote server and adding the new activity under the new activity category or at least one of the plurality of activity categories;
recording a new activity, via the at least one camera and adding the new activity under the new activity category or at least one of the plurality of activity categories; and
modifying at least one attribute associated with the plurality of activity categories, wherein the at least one attribute comprises name, priority, number of activities with an activity category, or display position.

19. A computer program product being embodied in a non-transitory computer readable storage medium of a computing device and comprising computer instructions for Artificial Intelligence (AI) assisted activity training, the computer program product comprising:

presenting, by a rendering device, a plurality of activity categories to a user, wherein each of the plurality of activity categories comprises a plurality of activities, and wherein the plurality of activity categories are presented as multimedia content;

receiving a voice-based input from the user, wherein the voice-based input comprises an activity training plan comprising a selection of at least one activity from at least one of the plurality of activity categories and at least one activity attribute associated with each of the at least one activity, and wherein the voice-based input is in a source language;

processing, by a Natural Language Processing (NLP) model, the received voice-based input to extract the selection of at least one activity and the at least one activity attribute, wherein the NLP model is configured using a single language, and wherein the single language is an intermediate language;

initiating, contemporaneous to receiving the voice-based input, presentation of a multimedia content in conformance with the at least one activity and the at least one activity attribute, wherein the multimedia content comprises a plurality of guidance steps performed by a virtual assistant corresponding to the at least one activity;

detecting, via at least one camera, initiation of a user activity performance of the user in response to initiation of the multimedia content, wherein the user activity performance of the user at a given time comprises imitation of one of the at least one activity;

capturing, via the at least one camera, a video of the user activity performance of the user, wherein the at least one camera is placed at distributed locations;

processing, in-real time, by an Artificial Intelligence (AI) model, the video to extract a set of user performance parameters of the user based on the user activity performance, wherein the set of user performance parameters comprises speed of a current activity performance, number of repetitions completed, overall completion of an activity circuit, third-party smart device information, pulse rate of the user, blood pressure of the user, and motion of the user;

generating, by the AI model, a feedback based on differential between the set of user performance parameters and a target set of performance parameters, wherein the target set of performance parameters comprises speed of the target activity performance, blood pressure, target number of repetitions, target pulse rate of the user, and target motion of the user;

rendering, contemporaneous to the user activity performance, the feedback to the user in at least one of an aural form, a visual form, or as haptic feedback.

* * * * *